US010214526B2

(12) United States Patent
Vakalopoulos et al.

(10) Patent No.: US 10,214,526 B2
(45) Date of Patent: Feb. 26, 2019

(54) SUBSTITUTED PYRAZOLO[1,5-A]-PYRIDINE-3-CARBOXAMIDES AND USE THEREOF

(71) Applicant: Bayer Pharma Aktiengesellschaft, Berlin (DE)

(72) Inventors: Alexandros Vakalopoulos, Hilden (DE); Damian Brockschnieder, Haan (DE); Frank Wunder, Wuppertal (DE); Johannes-Peter Stasch, Grottaferrata (IT); Tobias Marquardt, Wuppertal (DE); Lisa Dietz, Wuppertal (DE); Min Jian Volkhart Li, Velbert (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/548,158

(22) PCT Filed: Feb. 2, 2016

(86) PCT No.: PCT/EP2016/052126
§ 371 (c)(1),
(2) Date: Aug. 2, 2017

(87) PCT Pub. No.: WO2016/124565
PCT Pub. Date: Aug. 11, 2016

(65) Prior Publication Data
US 2018/0037580 A1 Feb. 8, 2018

(30) Foreign Application Priority Data

Feb. 5, 2015 (EP) .................................... 15153958

(51) Int. Cl.
C07D 471/04 (2006.01)
(52) U.S. Cl.
CPC ................. C07D 471/04 (2013.01)
(58) Field of Classification Search
CPC .................................................. C07D 471/04
See application file for complete search history.

(56) References Cited

U.S. PATENT DOCUMENTS

| 5,698,704 A | 12/1997 | Jackson |
| 6,180,656 B1 | 1/2001 | Fürstner et al. |
| 8,129,423 B2 | 3/2012 | Ackermann et al. |
| 8,969,045 B2 | 3/2015 | Burkhardt et al. |
| 9,126,998 B2 | 9/2015 | Vakalopoulos et al. |
| 2013/0210824 A1 | 8/2013 | Follmann et al. |
| 2014/0128425 A1 | 5/2014 | Vakalopoulos et al. |
| 2016/0010143 A1 | 1/2016 | Burkhardt et al. |

FOREIGN PATENT DOCUMENTS

| WO | 89/03833 A1 | 5/1989 |
| WO | 96/34866 A1 | 11/1996 |
| WO | 98/16223 A1 | 4/1998 |
| WO | 2008/061626 A1 | 5/2008 |
| WO | 2010/117787 A2 | 10/2010 |
| WO | 2010/123792 A1 | 10/2010 |
| WO | 2012/072512 A1 | 6/2012 |

OTHER PUBLICATIONS

Vippagunta et al. (2001).*
Artursson et al., "Correlation Between Oral Drug Absorption in Humans and Apparent Drug Permeability Coefficients in Human Intestinal Epithelial (CACO-2) Cells," Biochemical and Biophysical Research Communications, (Mar. 29, 1991, vol. 175, No. 3, pp. 880-885.
Bai et al., "Lewis Acid Catalyzed Intramolecular [4+2] and [3+2] Cross-Cycloaddition of Alkynylcyclopropane Ketones with Carbonyl Compounds and Imines," Angewandte Chemie International Edition, (Apr. 23, 2012), vol. 51, Issue 17, pp. 4112-4116.
Bergmann et al., "Autoxidation, of Hexaethylbenzene, 644. Organic Fluorine Compounds. Part XXVII.* Fluorinated α-Aminoisobutyric Acids," Journal of the Chemical Society, (1963), pp. 3462-3463.
Chen et al., "Radical Formation in the Oxidation of 2,2'-Azo-2-methyl-6-heptene by Thianthrene Cation Radical," The Journal of Organic Chemistry, (1996), vol. 61, No. 14, pp. 4716-4719.
Deng et al., "Studies on Phosphoroheterocycle Chemistry II: A Simple and New Route to 1,3,2-Diazaphospholidine-4-thione 2-sulfide Derivatives," Synthesis, (2001)), No. 16, pp. 2445-2449.
Fernandez et al. "Design, Synthesis and Structure-Activity-Relationship of 1,5-Tetrahydronaphthyridines as CETP Inhibitors," Bioorganic & Medicinal Chemistry Letters, (May 1, 2012), vol. 22, No. 9, pp. 3056-3062.
Freifelder et al., "Synthesis of Primary 1,2-Diamines by Hydrogenation of α-Aminonitriles," Journal of the American Chemical Society, (Feb. 1960), vol. 82, No. 3, pp. 696-698.
Glass et al., "Stimulation of Human Platelet Guanylate Cyclase by Fatty Acids," The Journal of Biological Chemistry, (Feb. 25, 1977), vol. 252, No. 4, pp. 1279-1285.
Hamill et al., "Improved Patch-Clamp Techniques for High-Resolution Current Recording from Cells and Cell-Free Membrane Patches," Pflügers Archiv, (1981), vol. 391, No. 2, pp. 85-100.
Hassan et al., "Aryl-Aryl Bond Formation One Century after the Discovery of the Ullmann Reaction," Chemical Reviews, (Mar. 8, 2002), vol. 102, No. 5, pp. 1359-1469.
Himmel et al., "Suitability of Commonly Used Excipients for Electrophysiological In-Vitro Safety Pharmacology Assessment of Effects on hERG Potassium Current and on Rabbit Purkinje Fiber Action Potential," Journal of Pharmacological and Toxicological Methods, (2007), vol. 56, No. 2, pp. 145-158.

(Continued)

Primary Examiner — Paul V Ward
(74) Attorney, Agent, or Firm — Ice Miller LLP

(57) ABSTRACT

The present application relates to novel substituted pyrazolo [1,5-a]pyridine-3-carboxamides, to processes for their preparation, to their use, alone or in combinations, for the treatment and/or prophylaxis of diseases, and to their use for producing medicaments for the treatment and/or prophylaxis of diseases, in particular for the treatment and/or prophylaxis of cardiovascular disorders.

18 Claims, No Drawings

(56) References Cited

OTHER PUBLICATIONS

Hiroi et al., "A Novel Method for Direct Construction of Indole Skeletons by Intramolecular Carbopalladation of Allenes Followed by Nucleophilic Substitution," Synlett, (2001, vol. 2001, No. 2, pp. 263-265.
Hjørringgaard et al., "An Automatic Solid-Phase Synthesis of Peptaibols," The Journal of Organic Chemistry, (2009), vol. 74, No. 3, pp. 1329-1332.
Hoenicka et al., "Purified Soluble Guanylyl Cyclase Expressed in a Baculovirus/Sf9 System: Stimulation by YC-1, Nitric Oxide, and Carbon Monoxide," Journal of Molecular Medicine, (Jan. 1999), vol. 77, No. 1, pp. 14-23.
Hossain et al., "Synthesis of Vicinal Diamino-Endo, Cis-Norbornene Derivatives," Synthetic Communications, (2012), vol. 42, No. 8, pp. 1200-1210.
Klapper et al., "Poly(Methykenamin)—Synthese Eines Polymers Mit Der Höchstmöglichen Zahl an Aminogruppen an Einer Polymeren Hauptkette," Angewandte Chemie, (Oct. 6, 2003), vol. 115, No. 38, pp. 4835-4838.
Ko et al., "YC-1, a Novel Activator of Platelet Guanylate Cyclase," Blood, (1994), vol. 84, No. 12, pp. 4226-4233.
Ko et al., "Universal Peptidomimetics," Journal of the American Chemical Society, (2011), vol. 133, No. 3, pp. 462-477.
Kojima et al., "Phosphodiesterase Inhibitors. Part 6: Design, Synthesis, and Structure-Activity Relationships of PDE4-Inhibitory Pyrazolo[1,5-α]Pyridines with Anti-Inflammatory Activity," Bioorganic & Medicinal Chemistry Letters, (Aug. 8, 2013), vol. 23, No. 19, pp. 5311-5316.
Kozo et al., "Spontaneous Hypertension in Rats," Int Rev. Exp. Pathol, (1969), vol. 7, pp. 227-270.
McConathy et al., "Radiolabeled Amino Acids for Tumor Imaging with PET: Radiosynthesis and Biological Evaluation of 2-Amino-3-[18F]Fluoro-2-Methylpropanoic Acid and 3-[18F]Fluoro-2-Methyl-2-(Methylamino Propanoic Acid," Journal of Medicinal Chemistry, (2002), vol. 45, No. 11, pp. 2240-2249.
Mello et al., "Reactions at Interfaces: Oxygenation of n-Butyl Ligands Anchored on Silica Surfaces with Methyl(trifluoromethyl)dioxirane," The Journal of Organic Chemistry, (2011) vol. 76, No. 24, pp. 10129-10139.
Mikami et al., "Applications of the Tandem [2,3]-Wittig-Oxy-Cope Rearrangement to Syntheses of exo-Brevicomin and Oxocrinol. The Scope and Limitation of the Sigmatropic Sequences as a Synthetic Method for δ,ε-Unsaturated Ketones," Chemistry Letters, (1982), vol. 11, No. 9, pp. 1349-1352.
Mülsch et al., "Effect of YC-1, an NO-independent, superoxide-sensitive stimulator of soluble guanylyl cyclase, on smooth muscle responsiveness to nitrovasodilators," British Journal of Pharmacology, (1997), vol. 120, No. 4, pp. 681-689.
Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.
Rubottom et al., "Preparation of Methyl Ketones by the Sequential Treatment of Carboxylic Acids with Methyllithium and Chlorotrimethylsilane," The Journal of Organic Chemistry, (1983), vol. 48, No. 9, pp. 1550-1552.
Scheel et al., "Introduction of a Modular Automated Voltage-Clamp Platform and Its Correlation with Manual Human Ether-à -go-go Related Gene Voltage-Clamp Data," ASSAY and Drug Development Technologies, (Dec. 2011), vol. 9, No. 6, pp. 600-607.
Scholz et al., "cis-1,2-Cyclobutandiamine Durch Photosensibilisierte Cyclo-Addition von 1,3-Diacetyl-4-Imidazolin-2-Onen an Olefine," European Journal of Organic Chemistry, Liebigs Ann. Chem., (Feb. 27, 1981), vol. 1981, No. 2, pp. 248-255.
Stasch et al., "Cardiovascular Actions of a Novel No-Independent Guanylyl Cyclase Stimulator, BAY 41/8543: in vivo Studies," British Journal of Pharmacology, (2002), vol. 135, No. 2, pp. 344-355.
Straub et al., "NO-Independent Stimulators of Soluble Guanylate Cyclase," Bioorganic & Medicinal Chemistry Letters, (Mar. 26, 2011), vol. 11, Issue 6, pp. 781-784.
Van Den Buuse, "Circadian Rhythms of Blood Pressure, Heart Rate, and Locomotor Activity in Spontaneously Hypertensive Rats as Measured with Radio-Telemetry," Physiology & Behavior, (Apr. 1994), vol. 55, Issue 4, pp. 783-787.
Von Der Saal et al., "Cyclopropandiamine, 4. Synthese und 1H-NMR-Spektren Diastereomerenreiner 1,2-Cyclopropandiamine und 1,2-Cyclopropandiammonium-dibromide," European Journal of Organic Chemistry, Liebigs Ann. Chem., (Jun. 13, 1994), vol. 1994, No. 6, pp. 569-579.
Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.
Wube et al., "Design, Synthesis and Antimycobacterial Activities of 1-Methyl-2-Alkenyl-4(1H)-Quinolones," Bioorganic & Medicinal Chemistry, (2011), vol. 19, No. 1, pp. 567-579.
Wunder et al., "A Cell-Based cGMP Assay Useful for Ultra-High-Throughput Screening and Identification of Modulators of the Nitric Oxide/cGMP Pathway," Analytical Biochemistry, (2005),vol. 339, No. 1, pp. 104-112.
Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 38, pp. 1587-1594.
Zhou et al., "Properties of HERG Channels Stably Expressed in HEK 293 Cells Studied at Physiological Temperature,"Biophysical Journal, (Jan. 1998), vol. 74, No. 1, pp. 230-241.
Notification of Transmittal of Translation of the International Preliminary Report on Patentability (Forms PCT/IB/338 and PCT/IB/373) and the Written Opinion of the International Searching Authority (Form PCT/ISA/237) dated Aug. 17, 2017, by the International Bureau of WIPO in corresponding International Application No. PCT/EP2016/052126. (6 pages).

* cited by examiner

SUBSTITUTED PYRAZOLO[1,5-A]-PYRIDINE-3-CARBOXAMIDES AND USE THEREOF

The present application relates to novel substituted pyrazolo[1,5-a]pyridine-3-carboxamides, to processes for their preparation, to their use, alone or in combinations, for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory centre. This is of central importance for the activation mechanism. NO is able to bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attacking the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

WO 2012/072512-A1 and WO 2010/117787, among other documents, disclose various pyrazolo[1,5-a]pyridine derivatives which can be used for treatment of disorders.

It was an object of the present invention to provide novel substances which act as stimulators of soluble guanylate cyclase and as such are suitable for the treatment and/or prophylaxis of diseases and have an identical or improved therapeutic profile compared to the compounds known from the prior art, for example with respect to their in vivo properties, for example their pharmacokinetic and pharmacodynamic characteristics, their solubility and/or their metabolic profile and/or their dose-activity relationship.

The present invention relates to compounds of the general formula (I)

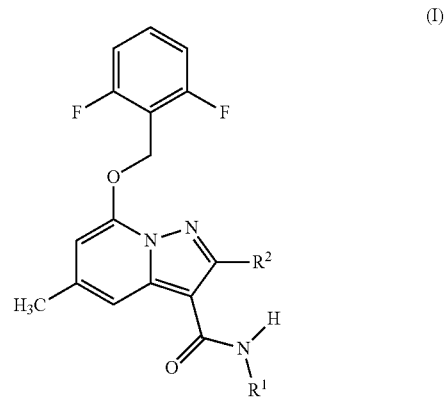

in which
$R^1$ represents a group of the formula

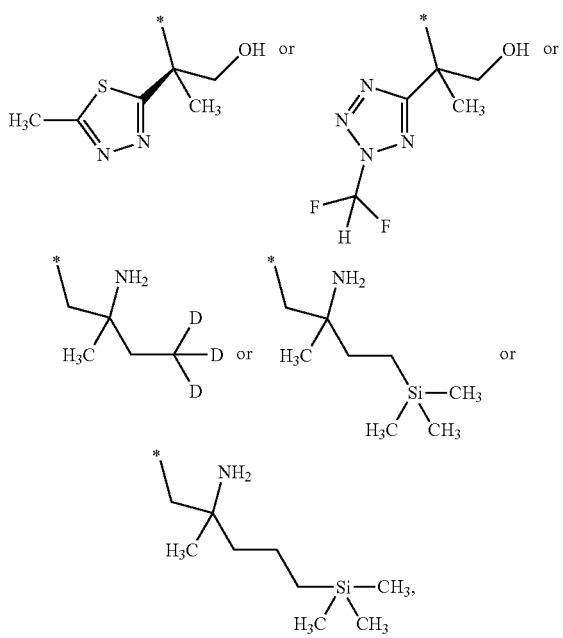

where * represents the point of attachment to the nitrogen atom, where
* represents the point of attachment to the nitrogen atom,
$R^2$ represents methyl or cyclopropyl, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated in a known manner from such mixtures of enantiomers and/or diastereomers; preference is given to using chromatographic methods for this purpose, in particular HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required, such modifications of the compounds according to the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents are defined as follows:

In the formulae of the group that $R^1$ may represent, the end point of the line marked by a * symbol does not represent a carbon atom or a $CH_2$ group but is part of the bond to the respective marked atom to which $R^1$ is attached.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which R¹ represents a group of the formula

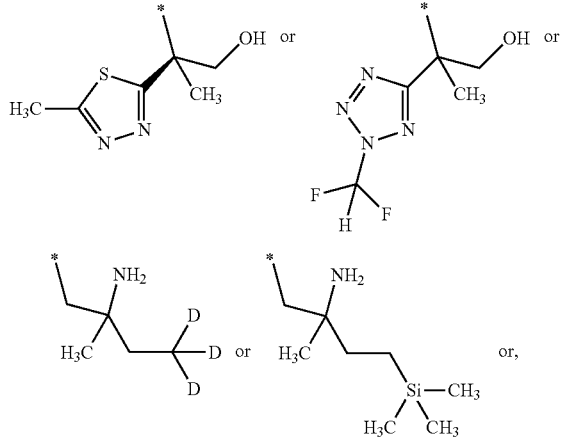

where * represents the point of attachment to the nitrogen atom, where
* represents the point of attachment to the nitrogen atom,
R² represents methyl, and the N-oxides, salts, solvates, salts of the N-oxides and solvates of the N-oxides and salts thereof.

In the context of the present invention, preference is given to the compound having the systematic name ent-7-[(2,6-difluorobenzyl)oxy]-N-[(2S)-1-hydroxy-2-(5-methyl-1,3,4-thiadiazol-2-yl)propan-2-yl]-2,5-dimethylpyrazolo[1,5-a]pyridine-3-carboxamide and the structural formula

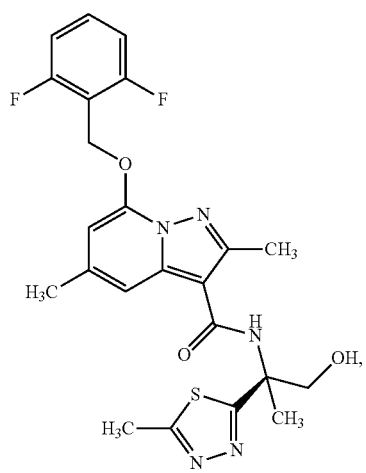 [SMILES: Cc1cc(OCc2c(F)cccc2F)n2nc(C)c(C(=O)N[C@@](C)(CO)c3nnc(C)s3)c2c1]

and to its salts, its solvates or the solvates of its salts.

In the context of the present invention, preference is given to the compound having the systematic name rac-7-[(2,6-difluorobenzyl)oxy]-N-{2-[2-(difluoromethyl)-2H-tetrazol-5-yl]-1-hydroxypropan-2-yl}-2,5-dimethylpyrazolo[1,5-a]pyridine-3-carboxamide and the structural formula

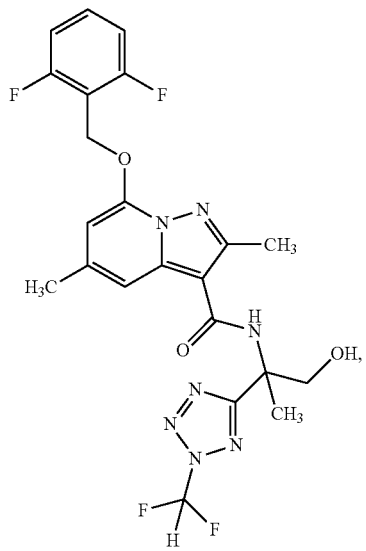 [SMILES: Cc1cc(OCc2c(F)cccc2F)n2nc(C)c(C(=O)NC(C)(CO)c3nnn(C(F)F)n3)c2c1]

and to its salts, its solvates or the solvates of its salts.

Preference in the context of the present invention is given to the compound having the systematic name ent-N-[2-amino-2-methyl(4,4,4-²H₃)butyl]-7-[(2,6-difluorobenzyl)oxy]-2,5-dimethylpyrazolo-[1,5-a]pyridine-3-carboxamide (enantiomer A) and the structural formula

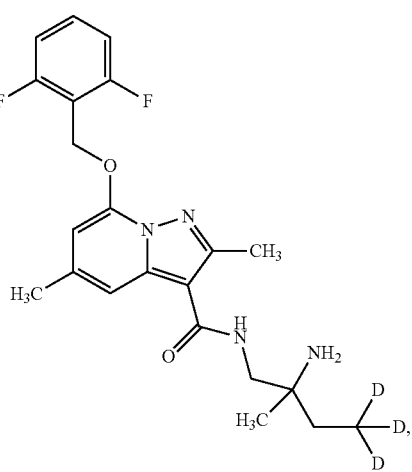

and to its salts, its solvates or the solvates of its salts.

Preference in the context of the present invention is given to the compound having the systematic name ent-N-[2-amino-2-methyl-4-(trimethylsilyl)butyl]-7-[(2,6-difluorobenzyl)oxy]-2,5-dimethylpyrazolo[1,5-a]pyridine-3-carboxamide (enantiomer A) and the structural formula

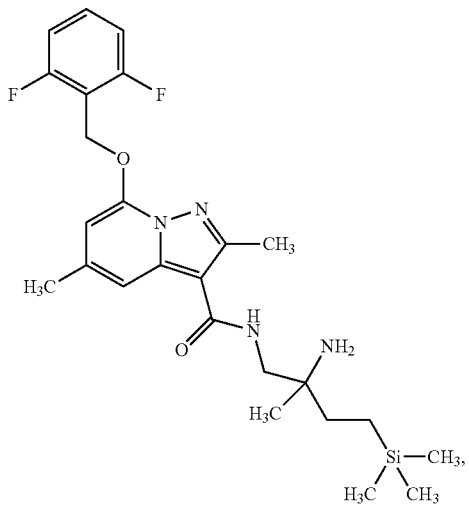 [SMILES: Cc1cc(OCc2c(F)cccc2F)n2nc(C)c(C(=O)NCC(C)(N)CC[Si](C)(C)C)c2c1]

and to its salts, its solvates or the solvates of its salts.

Preference in the context of the present invention is given to the compound having the systematic name ent-N-[2-amino-2-methyl-4-(trimethylsilyl)butyl]-7-[(2,6-difluorobenzyl)oxy]-2,5-dimethylpyrazolo[1,5-a]pyridine-3-carboxamide (enantiomer B) and the structural formula

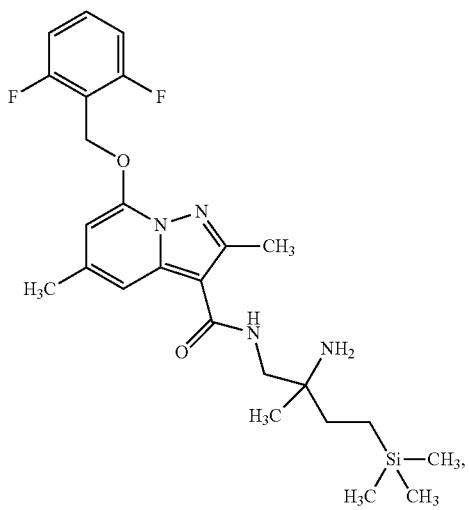 [SMILES: Cc1cc(OCc2c(F)cccc2F)n2nc(C)c(C(=O)NCC(C)(N)CC[Si](C)(C)C)c2c1]

and to its salts, its solvates or the solvates of its salts.

The radical definitions mentioned as being preferred apply both to the compounds of the formula (I) and correspondingly to all intermediates.

The invention furthermore provides a process for preparing the compounds of the formula (I) according to the invention, characterized in that a compound of the formula (II)

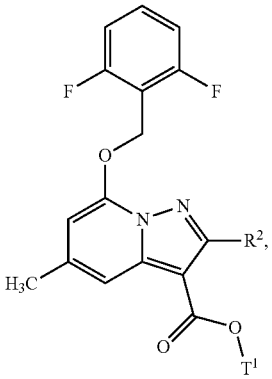

in which $R^2$ has the meaning given above and
$T^1$ represents $(C_1$-$C_4)$-alkyl or benzyl, is reacted in an inert solvent in the presence of a suitable base or acid to give a carboxylic acid of the formula (III)

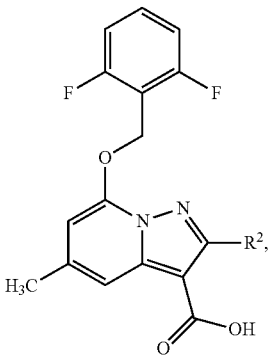

in which $R^2$ has the definition given above, and the latter are subsequently reacted, in an inert solvent under amide coupling conditions, with an amine of the formula (IV-A), (IV-B), (IV-C) or (IV-D)

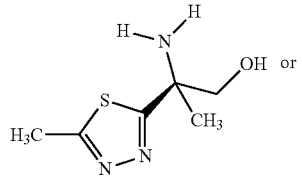

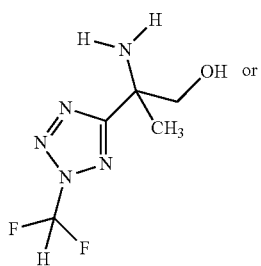

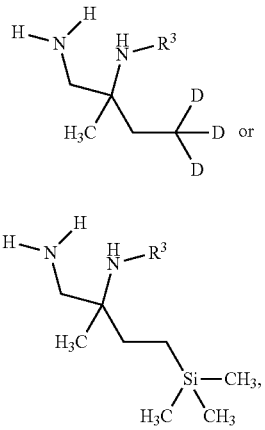

in which R³ represents an amino protecting group such as, for example, tert-butoxycarbonyl, benzyloxycarbonyl or benzyl, then any protective groups present are detached, and the resulting compounds of the formula (I) are optionally converted with the appropriate (i) solvents and/or (ii) acids or bases to the solvates, salts and/or solvates of the salts thereof.

The preparation process described can be illustrated by way of example by the following synthesis scheme (Scheme 1):

Scheme 1:

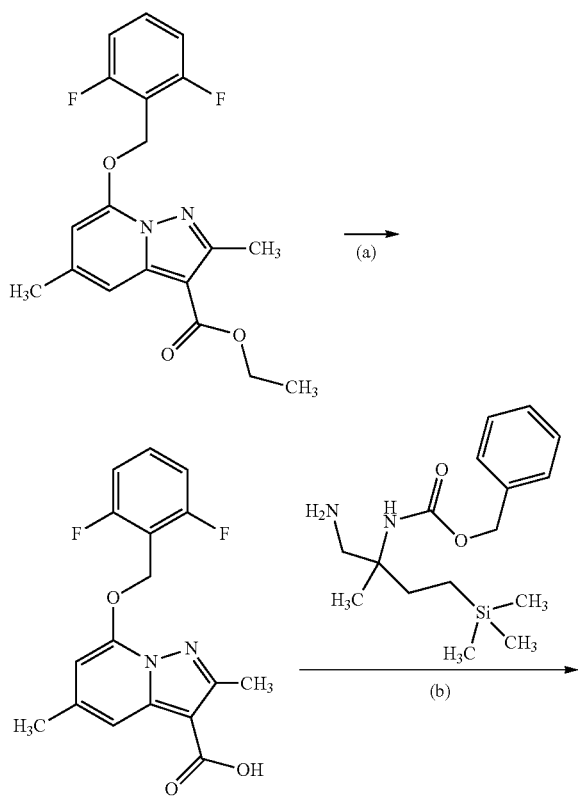

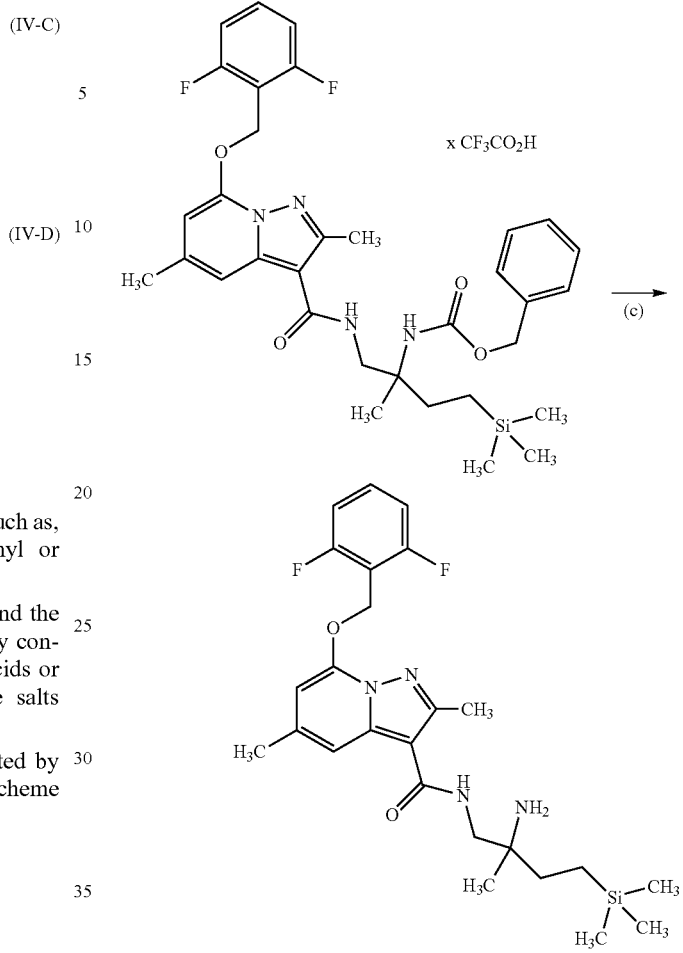

[(a) sodium hydroxide, 1,4-dioxane, 90° C.; (b) HATU, N,N-diisopropylethylamine, DMF, room temperature; (c) hydrogen, 10% palladium on activated carbon, TFA, ethanol].

The compounds of the formulae (IV-A), (IV-B), (IV-C) and (IV-D) are commercially available or known from the literature, or can be prepared in analogy to literature processes.

Inert solvents for the process steps (III)+(IV)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable for use as condensing agents for the amide formation in the process steps (III)+(IV)→(I) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline or isobutyl chloroformate, propanephosphonic anhydride (T3P), 1-chloro-N,N,2-trimethylprop-1-en-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, for example triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensation (III)+(IV)→(I) is generally conducted within a temperature range from −20° C. to +100° C., preferably at 0° C. to +60° C. The conversion can be effected at standard, elevated or reduced pressure (for example from 0.5 to 5 bar). In general, standard pressure pressure is employed.

Alternatively, the carboxylic acid of the formula (III) can also first be converted to the corresponding carbonyl chloride and the latter can then be converted directly or in a separate reaction with an amine of the formula (IV) to the compounds of the invention. The formation of carbonyl chlorides from carboxylic acids is carried out by the methods known to those skilled in the art, for example by treatment with thionyl chloride, sulfuryl chloride or oxalyl chloride, in the presence of a suitable base, for example in the presence of pyridine, and optionally with addition of dimethylformamide, optionally in a suitable inert solvent.

The hydrolysis of the ester group $T^1$ in the compounds of the formula (II) is carried out by customary methods, by treating the esters in inert solvents with acids or bases, in which latter case the salts formed at first are converted to the free carboxylic acids by treating with acid. In the case of the tert-butyl esters, the ester hydrolysis is preferably effected with acids. In the case of the benzyl esters, the ester cleavage is preferably carried out by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulfoxide. It is equally possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulfuric acid, hydrogen chloride/ hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, standard pressure is employed in each case.

The amino protecting group used is preferably tert-butoxycarbonyl (Boc) or benzyloxycarbonyl (Z). The protecting group used for a hydroxy or carboxyl function is preferably tert-butyl or benzyl. These protective groups are detached by customary methods, preferably by reaction with a strong acid such as hydrogen chloride, hydrogen bromide or trifluoroacetic acid in an inert solvent such as dioxane, diethyl ether, dichloromethane or acetic acid; it is optionally also possible to effect the detachment without an additional inert solvent. In the case of benzyl and benzyloxycarbonyl as protective groups, these may also be removed by hydrogenolysis in the presence of a palladium catalyst. The detachment of the protective groups mentioned can optionally be undertaken simultaneously in a one-pot reaction or in separate reaction steps.

The compounds of the formula (II) are known from the literature or can be prepared by

[A] reacting a compound of the formula (V)

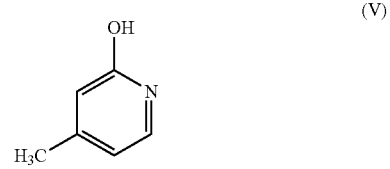

(V)

in an inert solvent in the presence of a suitable base with a compound of the formula (VI)

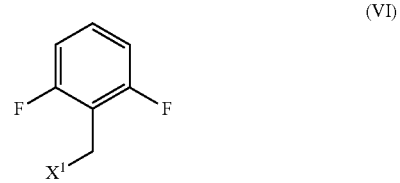

(VI)

in which $X^1$ represents a suitable leaving group, in particular chlorine, bromine, iodine, mesylate, triflate or tosylate, to give a compound of the formula (VII)

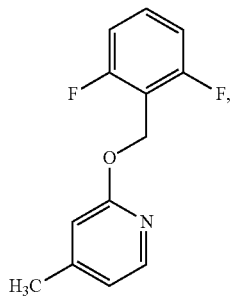
(VII)

then converting the latter with 0-(2-mesitylenesulfonyl)hydroxylamine (MSH) into a compound (VIII)

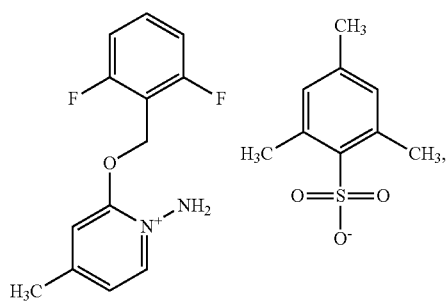
(VIII)

and then reacting this in an inert solvent with a compound of the formula (IX)

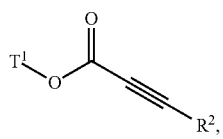
(IX)

in which $T^1$ and $R^2$ have the meanings given above,
or
[B] converting a compound of the formula (X)

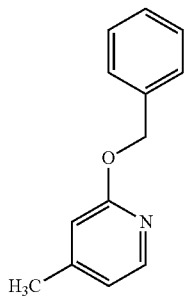
(X)

with O-(2-mesitylenesulphonyl)hydroxylamine (MSH) into a compound (XI)

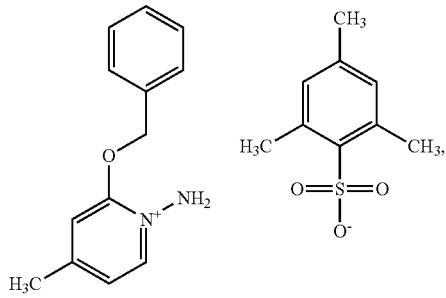
(XI)

then reacting this in an inert solvent with a compound of the formula (IX)

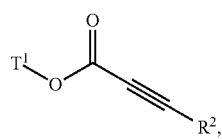
(IX)

in which $T^1$ and $R^2$ have the meaning given above, to give a compound (XII)

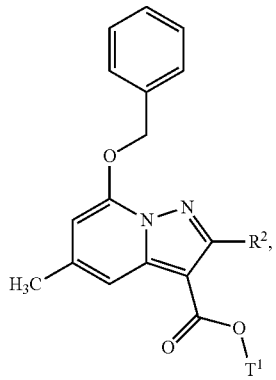
(XII)

in which $R^2$ has the meaning given above and
$T^1$ represents $(C_1\text{-}C_4)$-alkyl or benzyl,
subsequently detaching the benzyl group therefrom by the methods known to those skilled in the art and reacting the resulting compound (XIII)

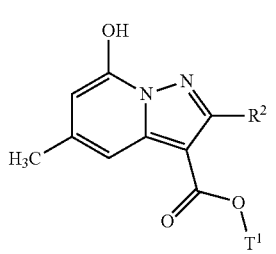
(XIII)

in which $R^2$ has the meaning given above and
$T^1$ represents $(C_1\text{-}C_4)$-alkyl or benzyl, in an inert solvent under Mitsunobu conditions with a compound of the formula (XIV)

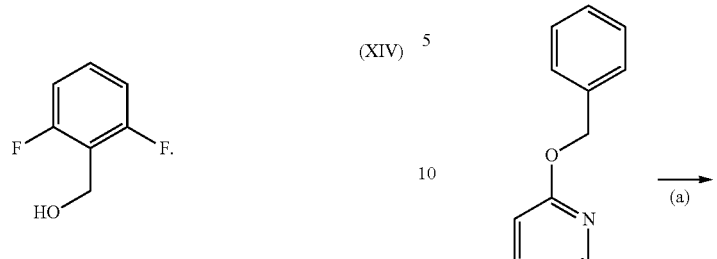

(XIV)

The processes described are illustrated by way of example by the schemes below (Schemes 2 to 3):

Scheme 2:

Scheme 3:

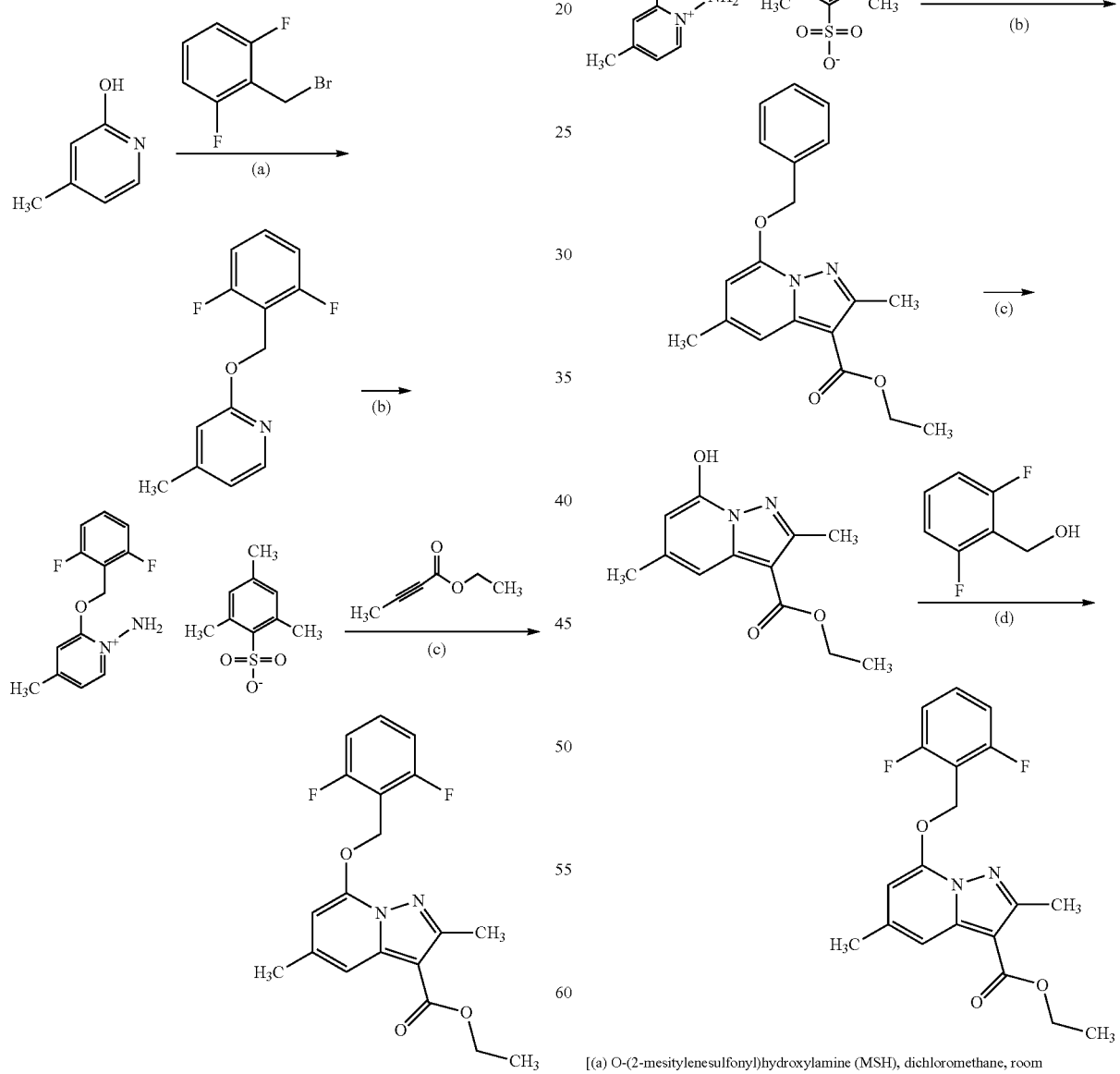

[(a) Ag$_2$CO$_3$, THF, reflux; (b) O-(2-mesitylenesulfonyl)hydroxylamine (MSH), dichloromethane, room temperature; (c) K$_2$CO$_3$, DMF, room temperature].

[(a) O-(2-mesitylenesulfonyl)hydroxylamine (MSH), dichloromethane, room temperature; (b) K$_2$CO$_3$, DMF, room temperature; (c) cyclohexene, Pd/C, ethanol, reflux; (d) triphenylphosphine, diisopropyl (E)-diazene-1,2-dicarboxylate (DIAD), THF, room temperature].

Inert solvents for the process step (V)+(VI)→(VII) are, for example, ethers such as diethyl ether, dioxane, tetrahydrofuran, dimethoxymethane, glycol dimethyl ether or diethylene glycol dimethyl ether, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP). It is equally possible to use mixtures of the solvents mentioned. Preference is given to using dimethoxyethane.

Suitable bases for the process step (V)+(VI)→(VII) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO). Preference is given to using sodium tert-butoxide or potassium tert-butoxide.

The reaction is generally carried out within a temperature range from 0° C. to +120° C., preferably at +20° C. to +80° C., optionally in a microwave. The reaction can be conducted at standard, elevated or reduced pressure (for example from 0.5 to 5 bar).

Inert solvents for the process step (VII)-(VIII) are, for example, dichloromethane, 1,2-dichloroethane, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP). It is equally possible to use mixtures of the solvents mentioned. Preference is given to using dichloromethane.

The reaction is generally carried out in a temperature range of from 0° C. to +120° C., preferably at +20° C. to +80° C. The reaction can be performed at atmospheric, elevated or reduced pressure (for example from 0.5 to 5 bar).

Inert solvents for the ring closure to give the imidazo[1,2-a]pyrazine base skeleton (VIII)+(IX)→(II) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulfoxide. It is equally possible to use mixtures of the solvents mentioned. Preference is given to using ethanol.

The ring closure is generally carried out within a temperature range from +50° C. to +150° C., preferably at +50° C. to +100° C., optionally in a microwave.

The ring closure (VIII)+(IX)→(II) is optionally effected in the presence of dehydrating reaction additives, for example in the presence of molecular sieve (pore size 3 Å or 4 Å) or by means of a water separator. The reaction (VIII)+(IX)→(II) is carried out using an excess of the reagent of the formula (VIII), for example with 1 to 20 equivalents of the reagent (VIII), optionally with addition of bases (for example sodium bicarbonate), in which case the addition of this reagent can take place all at once or in several portions.

The removal of the benzyl group in the reaction step (XII)→(XIII) is carried out here by customary methods known from protecting group chemistry, preferably by hydrogenolysis in the presence of a palladium catalyst, for example palladium on activated carbon, in an inert solvent, for example ethanol or ethyl acetate [see also, for example, T. W. Greene and P. G. M. Wuts, *Protective Groups in Organic Synthesis*, Wiley, New York, 1999].

The Mitsunobu condensation (XIII)+(XIV)→(II) is effected in the presence of an activating reagent, for example diethyl (E)-diazene-1,2-dicarboxylate (DEAD) or diisopropyl (E)-diazene-1,2-dicarboxylate (DIAD), and of a phosphine reagent, e.g. triphenylphosphine or tributylphosphine, in an inert solvent, e.g. THF, dichloromethane, toluene or DMF, at a temperature between 0° C. and the boiling point of the solvent used.

The compounds of the invention have valuable pharmacological properties and can be used for prevention and treatment of diseases in humans and animals. The compounds of the invention offer a further treatment alternative and thus enlarge the field of pharmacy.

The compounds according to the invention act as potent stimulators of soluble guanylate cyclase, have valuable pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in humans and animals.

The compounds of the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. Moreover, the compound according to the invention enhances the effect of substances increasing the cGMP concentration, such as, for example, EDRF (endothelium-derived relaxing factor), NO donors, protoporphyrin IX, arachidonic acid or phenylhydrazine derivatives.

The compounds of the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, elevated blood pressure (hypertension), resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic manifestations of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure and acute phases of worsening of existing chronic heart failure (worsening heart failure).

In addition, the compound according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinacmia, sitosterolaemia, xanthomatosis, Tangier disease, adiposity, obesity and of combined hyperlipidaemias and metabolic syndrome.

The compounds of the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds of the invention are also suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for the treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the compounds of the invention are also suitable for the treatment and/or prophylaxis of asthmatic disorders, pulmonary arterial hypertension (PAH) and other forms of pulmonary hypertension (PH) including left-heart disease-, HIV-, sickle cell anaemia-, thromboembolism- (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are effective agents for controlling migraine. They are also suitable for the prophylaxis and control of sequelae of cerebral infarct (Apoplexia cerebri) such as stroke, cerebral ischemias and skull-brain trauma. The compounds of the invention can likewise be used for controlling states of pain and tinnitus.

In addition, the compounds of the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds of the invention can also be used for the treatment and/or prophylaxis of autoimmune diseases.

The compounds of the invention are also suitable for the treatment and/or prophylaxis of fibrotic disorders of the internal organs, for example the lung, the heart, the kidney, the bone marrow and in particular the liver, and also dermatological fibroses and fibrotic eye disorders. In the context of the present inventions, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds of the invention are also suitable for controlling postoperative scarring, for example as a result of glaucoma operations.

The compounds of the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further provides for the use of the compounds of the invention for the treatment and/or prophylaxis of disorders, especially the disorders mentioned above.

The present invention further provides for the use of the compounds of the invention for the treatment and/or prophylaxis of heart failure, angina pectoris, hypertension, pulmonary hypertension, ischemias, vascular disorders, renal insufficiency, thromboembolic disorders, fibrotic disorders, arteriosclerosis, dementia disorders and erectile dysfunction.

The present invention further provides the compounds of the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds of the invention for production of a medicament for the treatment and/or prophylaxis of disorders, especially the disorders mentioned above.

The present invention further provides for the use of the compounds of the invention for preparing a medicament for the treatment and/or prophylaxis of heart failure, angina pectoris, hypertension, pulmonary hypertension, ischemias, vascular disorders, renal insufficiency, thromboembolic disorders, fibrotic disorders, arteriosclerosis, dementia disorders and erectile dysfunction.

The present invention further provides a method for the treatment and/or prophylaxis of disorders, in particular the disorders mentioned above, using an effective amount of at least one of the compounds of the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds of the invention.

The compounds according to the invention can be used alone or, if required, in combination with other active ingredients. The present invention further provides medicaments comprising at least one of the compounds of the invention and one or more further active compounds, especially for the treatment and/or prophylaxis of the aforementioned disorders. Preferred examples of suitable combination active ingredients include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances, hypotensive active compounds, by way of example and with preference from the group of the calcium antagonists, angiotensin AH antagonists, ACE inhibitors, endothelin antagonists, renin inhibitors, alpha-receptor blockers, beta-receptor blockers, mineralocorticoid receptor antagonists, and the diuretics; and/or active compounds altering lipid metabolism, by way of example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, dabigatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban (BAY 59-7939), edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, cartcolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan, embursartan, irbesartan, olmesartan, eprosartan or azilsartan or a dual angiotensin AII antagonist/NEP inhibitor, for example and with preference LCZ696 (valsartan/sacubitril).

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds of the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference dalcetrapib, BAY 60-5521, anacetrapib or CETP vaccine (CETi-1).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds of the invention can be converted to the administration forms mentioned. This can be accomplished in a manner known per se by mixing with inert, non-toxic, pharmaceutically suitable auxiliaries. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention.

Unless stated otherwise, the percentages in the tests and examples which follow are percentages by weight; parts are parts by weight. Solvent ratios, dilution ratios and concentration data for liquid/liquid solutions are based in each case on volume.

A. EXAMPLES

Abbreviations
abs. absolute (=dried)
aq. aqueous solution
calc. calculated
Boc tert-butyloxycarbonyl
br. broad signal (NMR coupling pattern)
CAS No. Chemical Abstracts Service number
Cbz benzyloxycarbonyl
δ shift in the NMR spectrum (stated in ppm)
d doublet (NMR coupling pattern)
TLC thin layer chromatography
DCI direct chemical ionization (in MS)
DMAP 4-N N-dimethylaminopyridine
DMF dimethylfonnamide
DMSO dimethyl sulfoxide
EDCI N-[3-(dimethylamino)propyl]-N'-ethylcarbodiimide
ent enantiomerically pure
eq. equivalent(s)
ESI electrospray ionization (in MS)
Et ethyl
h hour(s)
HATU N-[(dimethylamino)(3H-[1,2,3]triazolo[4,5-b]-pyridine-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
ID internal diameter
conc. concentrated
LC-MS liquid chromatography-coupled mass spectrometry
LiHMDS lithium hexamethyldisilazide
m multiplet
Me methyl
min minute(s)

MS mass spectrometry
NMR nuclear magnetic resonance spectrometry
PDA photodiode array detector
$Pd_2dba_3$ tris(dibenzylideneacetone)dipalladium
Ph phenyl
q quartet (NMR coupling pattern)
quint. quintet (NMR coupling pattern)
rac racemic
rel relative stereochemistry
$R_F$ retention factor (in thin-layer chromatography)
RT room temperature
$R_t$ retention time (in HPLC)
s singlet (NMR coupling pattern)
t triplet (NMR coupling pattern)
THF tetrahydrofuran
TBTU (benzotriazol-1-yloxy)bisdimethylaminomethylium fluoroborate
UPLC-MS ultra-pressure liquid chromatography-coupled mass spectrometry
UV ultraviolet spectrometry
v/v volume to volume ratio (of a solution)
Xantphos 4,5-bis(diphenylphosphino)-9,9-dimethylxanthene
XPHOS dicyclohexyl(2',4',6'-triisopropylbiphenyl-2-yl)phosphine LC-MS and HPLC Methods:

Method 1 (LC-MS):
Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm Method 2 (LC-MS):
Instrument: Waters ACQUITY SQD UPLC System; column: Waters Acquity UPLC HSS T3 1.8µ 50×1 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):
Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4 (Preparative HPLC):
Chromatorex C18 10µ 250×20 mm gradient: A=water+0.5% formic acid, B=acetonitrile, 0 min=5% B, 3 min=5% B pre-rinse without substance, then injection, 5 min=5% B, 25 min=30% B, 38 min=30% B, 38.1 min=95% B, 43.00 min=95% B, 43.01 min=5% B, 48.0 min=5% B; flow rate 20 ml/min, wavelength 210 nm.

Method 5 (Preparative HPLC):
Chromatorex C18 10µ 250×20 mm gradient: A=water+0.5% formic acid, B=acetonitrile, 0 min=5% B, 3 min=5% B pre-rinse without substance, then injection, 5 min=5% B, 25 min=50% B, 38 min=50% B, 38.1 min=95% B, 43.00 min=95% B, 43.01 min=5% B, 48.0 min=5% B; flow rate 20 ml/min, wavelength 210 nm.

Method 6 (Preparative HPLC):
XBridge Prep. C18 5µ 50×19 mm gradient: A=water+0.5% ammonium hydroxide, B=acetonitrile, 0 min=5% B, 3 min=5% B pre-rinse without substance, then injection, 5 min=5% B, 25 min=50% B, 38.0 min=50% B, 38.1 min=95% B, 43.00 min=95% B, 43.01 min=5% B, 48.0 min=5% B; flow rate 15 ml/min, wavelength 210 nm.

Method 7 (LC-MS):
MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 8 (LC-MS):
Instrument: Waters ACQUITY SQD UPLC System; column: Waters Acquity UPLC HSS T3 1.8µ 30×2 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 9 (Preparative HPLC):
MS instrument: Waters, HPLC instrument: Waters (column Waters X-Bridge C18, 18 mm×50 mm, 5 µm, eluent A: water+0.05% triethylamine, mobile phase B: acetonitrile (ULC)+0.05% triethylamine, with gradient; flow rate: 40 ml/min; UV detection: DAD; 210-400 nm) or:
MS instrument: Waters, HPLC instrument: Waters (column Phenomenex Luna 5µ C18(2) 100A, AXIA Tech. 50×21.2 mm, eluent A: water+0.05% formic acid, mobile phase B: acetonitrile (ULC)+0.05% formic acid, with gradient; flow rate: 40 ml/min; UV detection: DAD; 210-400 nm).

Method 10 (LC-MS):
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method 11 (MS):
Instrument: Waters ZQ 2000; electrospray ionization; mobile phase A: 1 l of water+0.25 ml of 99% strength formic acid; mobile phase B: 1 l of acetonitrile+0.25 ml of 99% strength formic acid; 25% A, 75% B; flow rate: 0.25 ml/min.

Method 12 (DCI-MS):
Instrument: Thermo Fisher-Scientific DSQ; chemical ionization; reactant gas $NH_3$; source temperature: 200° C.; ionization energy 70 eV.

Method 13 (LC-MS):
MS instrument: Waters (Micromass) Quattro Micro; HPLC instrument: Agilent 1100 series; column: YMC-Triart C18 3µ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 14 (GC-MS):
Instrument: Thermo Scientific DSQII, Thermo Scientific Trace GC Ultra; column: Restek RTX-35MS, 15 m×200 µm×0.33 µm; constant flow rate with helium: 1.20 ml/min; oven: 60° C.; inlet: 220° C.; gradient: 60° C., 30° C./min→300° C. (maintain for 3.33 min).

Method 15 (LC-MS, Analytical):
Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid; mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 16 (LC-MS, Analytical):

MS instrument: Waters (Micromass) Quattro Micro; instrument Waters UPLC Acquity; column: Waters BEH C18 1.7μ 50×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 17 (LC-MS):

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Further Details:

In the case of purifications of compounds of the invention by preparative HPLC by the above-described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Thus, the trifluoroacetate, formate or ammonium salts can be converted into the salt-free form by extracting an organic solution or suspension with saturated aqueous sodium bicarbonate solution.

Furthermore, amidines can be present as free compounds or partially (depending on the preparation if acetic acid is involved) as acetate salts or acetate solvates.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride". "trifluoroacetate", "sodium salt" or "x HCl", "x CF₃COOH", "x Na⁺" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Furthermore, the secondary amides according to the invention may be present as rotational isomers/isomer mixtures, in particular in NMR studies. Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

In all $^1$H NMR spectra data, the chemical shifts S are stated in ppm.

The multiplicities of proton signals in $^1$H NMR spectra reported in the paragraphs which follow represent the signal form observed in each case and do not take account of any higher-order signal phenomena. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

In $^1$H NMR spectra, the methyl group of the chemical system "2-methylpyrazolo[1,5-a]pyridine" appears as a singlet (frequently in DMSO-$d_6$ and in the range of 2.40-2.60 ppm) and is clearly distinguishable as such, is superposed by the solvent signals or is completely under the signals of the solvents.

Melting points and melting point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates

Example 1A

2-[(2,6-Difluorobenzyl)oxy]-4-methylpyridine

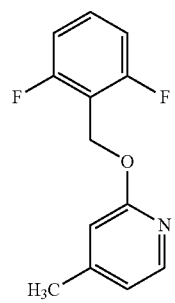

A mixture of 5.00 g (24.2 mmol, 1.0 eq.) of 2,6-difluorobenzyl bromide [CAS No: 85118-00-9] and 3.16 g (29.0 mmol, 1.2 eq.) of 2-hydroxy-4-methylpyridine [CAS No: 13466-41-6] was dissolved in 50 ml of THF. 7.99 g (29.0 mmol, 1.2 eq.) of silver carbonate were added to the solution, and the mixture was heated at reflux with exclusion of light overnight. Subsequently, the reaction mixture was filtered through kieselguhr, eluting with ethyl acetate, and the filtrate was concentrated. The crude product was purified by means of Biotage Isolera (100 g silica gel cartridge, cyclohexane/ethyl acetate gradient, 0% to 10% ethyl acetate). This gave 3.51 g of the title compound (61% of theory).

TLC (silica gel, cyclohexane/ethyl acetate 10:1): $R_F$=0.50
LC-MS (Method 2): $R_t$=1.17 min
MS (ESpos): m/z=236 (M+H)$^+$
$^1$H-NMR (400 MHz, DMSO-d$_6$): δ [ppm]=2.26 (s, 3H), 5.35 (s, 2H), 6.66 (s, 1H), 6.86 (d, 1H), 7.12-7.21 (m, 2H), 7.47-7.56 (m, 1H), 8.06 (d, 1H).

Example 2A

1-Amino-2-[(2,6-difluorobenzyl)oxy]-4-methylpyridinium 2,4,6-trimethylbenzenesulfonate

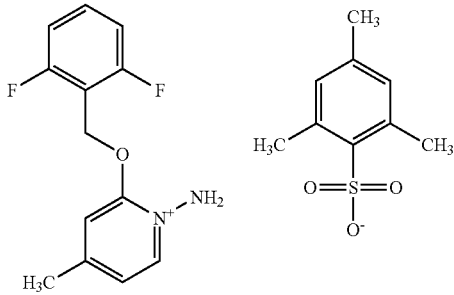

A mixture of 3.4 ml (43.9 mmol, 10 eq.) of trifluoroacetic acid and 0.33 ml of water was cooled to −5° C. At this temperature, 1.88 g (6.59 mmol, 1.5 eq.) of ethyl (1E)-N-[(mesitylsulfonyl)oxy]ethanimidoate [CAS No: 38202-27-6] were added a little at a time. After 1.5 h, 30 ml of ice-water were added, the mixture was stirred briefly, and the resulting O-(2-mesitylenesulfonyl)hydroxylamine (MSH) was filtered off using a precooled frit and washed with 30 ml of ice-water. The water-moist O-(2-mesitylenesulfonyl)hydroxylamine was dissolved in 12 ml of dichloromethane, dried with magnesium sulfate and filtered, and the filtrate was added dropwise directly to a solution of 1.03 g (4.39 mmol, 1.0 eq.) of 2-[(2,6-difluorobenzyl)oxy]-4-methylpyridine from Example 1A in 2 ml of dichloromethane. The mixture was stirred at RT overnight. Subsequently, diethyl ether was added dropwise, and the precipitate obtained was filtered off, washed with diethyl ether and dried. 1.3 g of the title compound were isolated (59% of theory, purity 90%).
$^1$H-NMR (400 MHz, DMSO-d$_6$): δ [ppm]=2.17 (s, 3H), 2.46-2.57 (s, 3H and s, 6H superposed by the solvent signal), 5.64 (s, 2H), 6.74 (s, 2H), 7.23-7.48 (m, 4H), 7.60-7.70 (m, 1H), 7.86 (br s, 1H), 8.44 (d, 1H).

Example 3A

Ethyl 7-[(2,6-difluorobenzyl)oxy]-2,5-dimethylpyrazolo[1,5-a]pyridine-3-carboxylate

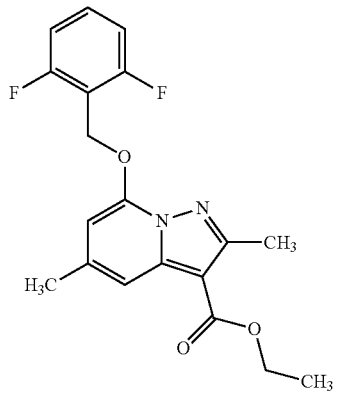 [SMILES: CCOC(=O)c1c(C)nn2c(OCc3c(F)cccc3F)cc(C)cc12]

1.62 g (3.60 mmol, 1.0 eq.) of 1-amino-2-[(2,6-difluorobenzyl)oxy]-4-methylpyridinium 2,4,6-trimethylbenzenesulfonate from Example 2A were dissolved in 36 ml of DMF, and 0.84 ml (7.19 mmol, 2.0 eq.) of ethyl but-2-ynoate [CAS No: 4341-76-8] were added. 0.994 g (7.19 mmol, 2.0 eq.) of potassium carbonate was added and the mixture was stirred at RT for 1.5 h. Subsequently, the mixture was poured onto 150 ml of water and stirred briefly, and the resulting solid was filtered off, washed with water and dried. This gave 440 mg of the title compound (45% of theory, 87%).
LC-MS (Method 2): $R_t$=1.22 min
MS (ESpos): m/z=361 (M+H)$^+$

Example 4A

7-[(2,6-Difluorobenzyl)oxy]-2,5-dimethylpyrazolo[1,5-a]pyridine-3-carboxylic acid

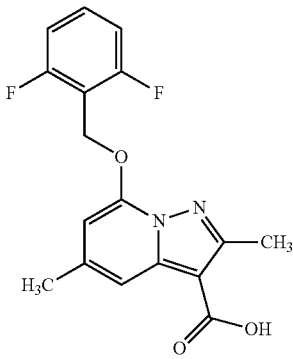 [SMILES: Cc1cc(OCc2c(F)cccc2F)n2nc(C)c(C(=O)O)c2c1]

4.9 ml (4.88 mmol, 4.0 eq.) of 1 N aqueous sodium hydroxide solution were added to a solution of 0.440 g (1.22 mmol, 1 eq.) of ethyl 7-[(2,6-difluorobenzyl)oxy]-2,5-dimethylpyrazolo[1,5-a]pyridine-3-carboxylate from Example 3A in 12.7 ml of dioxane, and the mixture was stirred at 90° C. for 36 h. Subsequently, the reaction mixture was concentrated and the resulting solid was filtered off. The filtrate was acidified with 6 N aqueous hydrochloric acid and stirred briefly. The solid formed was filtered off, washed with water and dried. This gave 248 mg of the title compound (61% of theory, purity 60%), which was converted further without further purification.
LC-MS (Method 2): $R_t$=0.96 min
MS (ESpos): m/z=333 (M+H)$^+$

Example 5A rac-2-Amino-2-methyl(4,4,4-$^2$H$_3$)butanonitrile

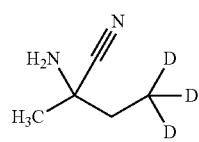

2.0 g (26.62 mmol) of (4,4,4-$^2$H$_3$)butan-2-one [CAS Registry Number: 53389-26-7] were initially charged in 22.3 ml of 2 N ammonia in methanol, and 1.72 g (35.14 mmol) of sodium cyanide and 1.88 g (35.14 mmol) of ammonium chloride were added at room temperature and the mixture was stirred under reflux for 4 hours. The reaction mixture was cooled, 40 ml of diethyl ether were added and the solid present was filtered off. The solvent was distilled out of the filtrate under standard pressure. 2.75 g of the title compound (51% of theory at a purity of about 50%) were obtained as residue, which was used in the subsequent stage without further purification.

GC-MS (Method 14): $R_t$=1.66 min

MS (ESpos): m/z=86 (M-CH$_3$)$^+$

Example 6A rac-Benzyl [2-cyano(4,4,4-$^2$H$_3$)butan-2-yl]carbamate

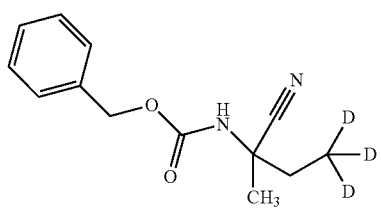 [SMILES: [2H]C([2H])([2H])CC(C)(C#N)NC(=O)OCc1ccccc1]

2.75 g (13.59 mmol at a purity of about 50%) of rac-2-amino-2-methyl(4,4,4-$^2$H$_3$)butanonitrile from Example 5A were initially charged in 33 ml of tetrahydrofuran/water=9/1, and 5.82 g (42.13 mmol) of potassium carbonate were added. At 0° C., 2.32 g (13.59 mmol) of benzyl chloroformate were slowly added dropwise. Then the mixture was allowed to warm up gradually to room temperature with stirring, and was stirred at room temperature overnight. The supernatant solvent was decanted off, the residue was twice stirred with 25 ml each time of tetrahydrofuran, and then the supernatant solvent was decanted off each time. The combined organic phases were concentrated and the crude product was purified by silica gel chromatography (mobile phase gradient: cyclohexane to cyclohexane/dichloromethane gradient 1/1 to 1/2). This gave 2.56 g of the title compound (78% of theory).

LC-MS (Method 2): $R_t$=0.89 min

MS (ESpos): m/z=236 (M+H)$^+$ $^1$H-NMR (400 MHz, DMSO-d$_6$): δ [ppm]=1.51 (s, 3H), 1.75-1.91 (m, 2H), 5.08 (s, 2H), 7.28-7.42 (m, 5H), 7.96 (br. s, 1H).

Example 7A ent-Benzyl-[2-cyano(4,4,4-$^2$H$_3$)butan-2-yl]carbamate (Enantiomer A)

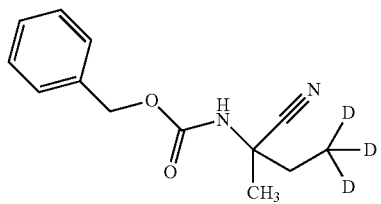 [SMILES: [2H]C([2H])([2H])CC(C)(C#N)NC(=O)OCc1ccccc1]

2.56 g of rac-benzyl [2-cyano(4,4,4-$^2$H$_3$)butan-2-yl]carbamate from Example 6A were separated into the enantiomers by preparative separation on a chiral phase [column: Daicel Chiralcel OJ-H, 5 μm, 250×20 mm, mobile phase: 70% isohexane, 30% isopropanol, flow rate: 15 ml/min, temperature: 47° C., detection: 220 nm].

Enantiomer A: 1.03 g (>99% ee)

$R_t$=7.11 min [Daicel Chiralcel OJ-H, 250×4.6 mm, 5 μm, mobile phase: 70% isohexane, 30%, isopropanol, flow rate: 1 ml/min, temperature: 50° C., detection: 220 nm].

Example 8A ent-Benzyl [2-cyano(4,4,4-$^2$H$_3$)butan-2-yl]carbamate (Enantiomer B)

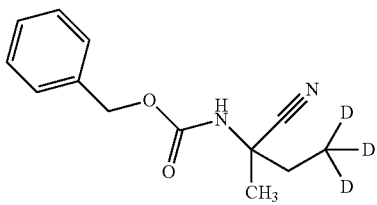 [SMILES: [2H]C([2H])([2H])CC(C)(C#N)NC(=O)OCc1ccccc1]

2.56 g of rac-benzyl [2-cyano(4,4,4-$^2$H$_3$)butan-2-yl]carbamate from Example 6A were separated into the enantiomers by preparative separation on a chiral phase [column: Daicel Chiralcel OJ-H, 5 μm, 250×20 mm, mobile phase: 70% isohexane, 30% isopropanol, flow rate: 15 ml/min, temperature: 47° C., detection: 220 nm].

Enantiomer B: 0.99 g (>99% ee)

$R_t$=8.25 min [Daicel Chiralcel OJ-H, 250×4.6 mm, 5 μm, mobile phase: 70% isohexane, 30% isopropanol, flow rate: 1 ml/min, temperature: 50° C., detection: 220 nm].

Example 9A ent-Benzyl [1-amino-2-methyl(4,4,4-$^2$H$_3$)butan-2-yl]carbamate (Enantiomer A)

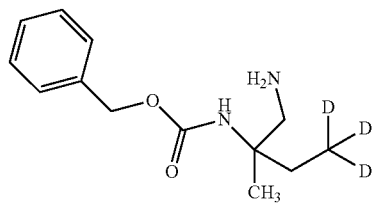 [SMILES: [2H]C([2H])([2H])CC(C)(CN)NC(=O)OCc1ccccc1]

0.50 g (2.13 mmol) of ent-benzyl [2-cyano(4,4,4-$^2$H$_3$)butan-2-yl]carbamate (enantiomer A) from Example 7A were dissolved in 10 ml of 7 N ammonia solution in methanol, and 0.79 g of Raney nickel (50% aqueous slurry) were added under argon. The reaction mixture was hydrogenated in an autoclave at 20-30 bar for 3 h. The reaction mixture was filtered through kieselguhr, rinsed with methanol and concentrated. This gave 387 mg (75% of theory) of the target compound which was used without further purification for the next step.

LC-MS (Method 2): $R_t$=0.50 min

MS (ESpos): m/z=240 (M+H)$^+$

Example 10A ent-Benzyl [1-amino-2-methyl(4,4,4-²H₃)butan-2-yl] carbamate (Enantiomer B)

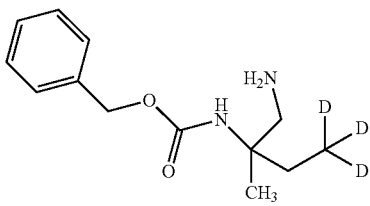 [SMILES: [2H]C([2H])([2H])CC(C)(CN)NC(=O)OCc1ccccc1]

0.50 g (2.13 mmol) of ent-benzyl [2-cyano(4,4,4-²H₃) butan-2-yl]carbamate (enantiomer B) from Example 8A were dissolved in 10 ml of 7 N ammonia solution in methanol, and 0.79 g of Raney nickel (50% aqueous slurry) were added under argon. The reaction mixture was hydrogenated in an autoclave at 20-30 bar for 3 h. The reaction mixture was filtered through kieselguhr, rinsed with methanol and concentrated. This gave 487 mg (94% of theory) of the target compound which was used without further purification for the next step.

LC-MS (Method 2): $R_t$=0.53 min
MS (ESpos): m/z=240 (M+H)⁺

Example 11A rac-2-Amino-2-methyl-4-(trimethylsilyl)butanonitrile

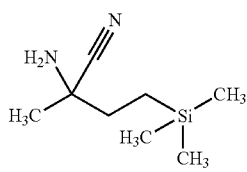

13.0 g (90.10 mmol) of 4-(trimethylsilyl)butan-2-one [commercially available or synthetically available according to R. Acerete et al. Journal of Organic Chemistry 2011, 76, 10129-10139] were initially charged in 25 ml of 7 N ammonia in methanol, 5.83 g (118.93 mmol) of sodium cyanide and 6.36 g (118.93 mmol) of ammonium chloride were added at room temperature and the mixture was stirred under reflux for 3 hours. The reaction mixture was cooled and the solid present was filtered off. The filtrate was used for the next step without further purification.

Example 12A rac-Benzyl [2-cyano-4-(trimethylsilyl)butan-2-yl] carbamate

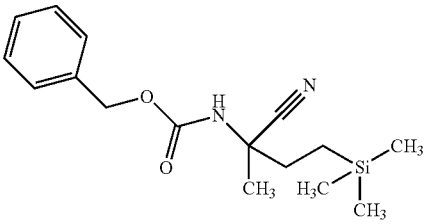 [SMILES: CC(C#N)(CC[Si](C)(C)C)NC(=O)OCc1ccccc1]

The crude solution of rac-2-amino-2-methyl-4-(trimethylsilyl)butanonitrile from Example 11A was initially charged in 16 ml of water, and 37.36 g (270.35 mmol) of potassium carbonate were added. At 0° C., 23.06 g (135.18 mmol) of benzyl chloroformate were slowly added dropwise. Then the mixture was allowed to warm up gradually to room temperature with stirring, and was stirred at room temperature overnight. The reaction mixture was filtered and the residue was washed repeatedly with tetrahydrofuran. The filtrate was concentrated and the crude product was purified by silica gel chromatography (mobile phase: cyclohexane/ethyl acetate=9/1). This gave 11.60 g of the title compound (42% of theory over two steps).

LC-MS (Method 2): $R_t$=1.23 min
MS (ESpos): m/z=305 (M+H)⁺
¹H-NMR (400 MHz, DMSO-d₆): δ [ppm]=−0.01 (s, 9H), 0.45-0.67 (m, 2H), 1.52 (s, 3H), 1.73-1.90 (m, 2H), 2.24-2.52 (m, 2H), 5.08 (s, 2H), 7.29-7.44 (m, 5H), 7.94 (br. s, 1H).

Example 13A ent-Benzyl [2-cyano-4-(trimethylsilyl)butan-2-yl] carbamate (Enantiomer A)

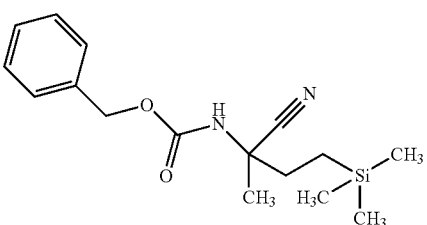

10.0 g of rac-benzyl [2-cyano-4-(trimethylsilyl)butan-2-yl]carbamate from Example 12A were separated into the enantiomers by preparative separation on a chiral phase [column: Daicel Chiralpak AY-H, 5 μm, 250×20 mm, mobile phase: 15% ethanol, 85% isohexane, flow rate: 20 ml/min, temperature: 30° C., detection: 220 nm].

Enantiomer A: 4.19 g (>99% ee)

$R_t$=5.24 min [Daicel Chiralpak AY-H, 250×4.6 mm, 5 μm, mobile phase: 10% ethanol, 90% isohexane, flow rate: 1 ml/min, temperature: 45° C., detection: 220 nm].

Example 14A ent-Benzyl [2-cyano-4-(trimethylsilyl)butan-2-yl] carbamate (Enantiomer B)

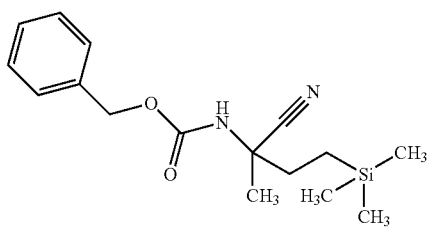 [SMILES: CC(C#N)(CC[Si](C)(C)C)NC(=O)OCc1ccccc1]

10.0 g of rac-benzyl [2-cyano-4-(trimethylsilyl)butan-2-yl]carbamate from Example 12A were separated into the enantiomers by preparative separation on a chiral phase [column: Daicel Chiralpak AY-H, 5 µm, 250×20 mm, mobile phase: 15% ethanol, 85% isohexane, flow rate: 20 ml/min, temperature: 30° C., detection: 220 nm].

Enantiomer B: 4.24 g (>99% ee)

$R_t$=6.89 min [Daicel Chiralpak AY-H, 250×4.6 mm, 5 µm, mobile phase: 10% ethanol, 90% isohexane, flow rate: 1 ml/min, temperature: 45° C., detection: 220 nm].

Example 15A ent-Benzyl [1-amino-2-methyl-4-(trimethylsilyl) butan-2-yl]carbamate (Enantiomer A)

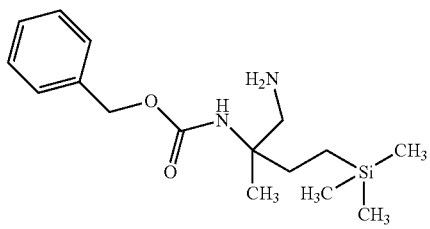

2.0 g (6.57 mmol) of ent-benzyl [2-cyano-4-(trimethylsilyl)butan-2-yl]carbamate (enantiomer A) from Example 13A were dissolved in 31 ml of 7 N ammonia solution in methanol, and 2.44 g of Raney nickel (50% aqueous slurry) were added under argon. The reaction mixture was hydrogenated in an autoclave at 20-30 bar for 3 h. The reaction mixture was filtered through kieselguhr, rinsed with methanol and concentrated. This gave 1.80 g (87% of theory) of the target compound which was used without further purification for the next step.

LC-MS (Method 16): $R_t$=1.66 min
MS (ESpos): m/z=309 (M+H)$^+$

Example 16A ent-Benzyl [1-amino-2-methyl-4-(trimethylsilyl) butan-2-yl]carbamate (Enantiomer B)

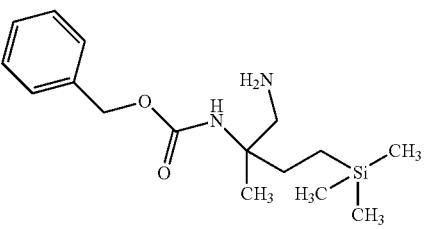 [SMILES: CC(CN)(CC[Si](C)(C)C)NC(=O)OCc1ccccc1]

2.0 g (6.57 mmol) of ent-benzyl [2-cyano-4-(trimethylsilyl)butan-2-yl]carbamate (enantiomer B) from Example 14A were dissolved in 31 ml of 7 N ammonia solution in methanol, and 2.44 g of Raney nickel (50% aqueous slurry) were added under argon. The reaction mixture was hydrogenated in an autoclave at 20-30 bar for 3 h. The reaction mixture was filtered through kieselguhr, rinsed with methanol and concentrated. This gave 1.72 g (83% of theory) of the target compound which was used without further purification for the next step.

LC-MS (Method 2): $R_t$=0.78 min
MS (ESpos): m/z=309 (M+H)$^+$

Example 17A ent-Benzyl {1-[({7-[(2,6-difluorobenzyl)oxy]-2,5-dimethylpyrazolo[1,5-a]pyridin-3-yl}carbonyl) amino]-2-methyl(4,4,4-$^2$H$_3$)butan-2-yl}carbamate (Enantiomer A)

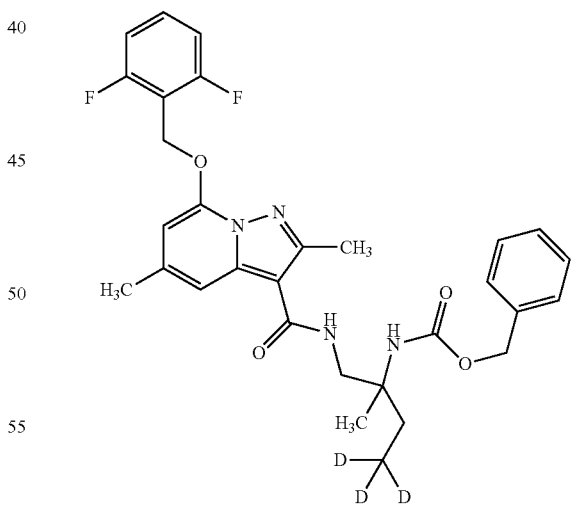

75 mg (0.19 mmol, purity 84%) of 7-[(2,6-difluorobenzyl)oxy]-2,5-dimethylpyrazolo[1,5-a]pyridine-3-carboxylic acid from Example 4A were initially charged together with 87 mg (0.23 mmol) of HATU and 0.1 ml (0.57 mmol) of N,N-diisopropylethylamine in 0.70 ml of DMF, and the mixture was stirred at room temperature for 10 min. Subsequently, 60 mg (0.25 mmol) of ent-benzyl-[1-amino-2-methyl(4,4,4-$^2$H$_3$)butan-2-yl]carbamate (enantiomer A)

from Example 9A were added to the reaction solution and the mixture was stirred at RT overnight. Another 23 mg (0.095 mmol) of ent-benzyl-[1-amino-2-methyl(4,4,4-$^2H_3$)butan-2-yl]carbamate (enantiomer A) were added and the mixture was stirred at RT for 1 h. 7 ml of water were then added to the mixture. The precipitate formed was filtered off and dried under high vacuum. This gave 111 mg of the target compound (80% of theory, purity 76%).

LC-MS (Method 2): $R_t$=1.17 min

MS (ESpos): m/z=554 (M+H)$^+$

Example 18A ent-Benzyl {1-[({7-[(2,6-difluorobenzyl)oxy]-2,5-dimethylpyrazolo[1,5-a]pyridin-3-yl}carbonyl)amino]-2-methyl-4-(trimethylsilyl)butan-2-yl}carbamate trifluoroacetate (Enantiomer A)

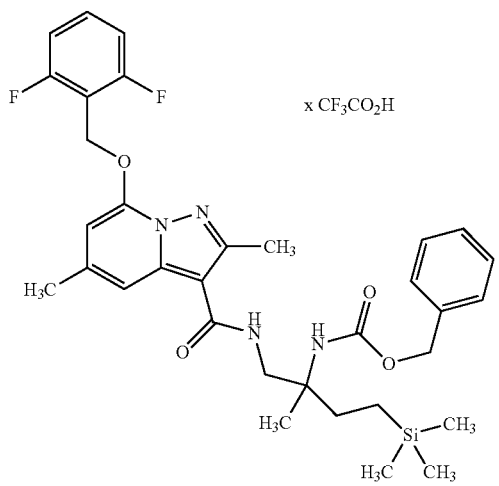 [SMILES: Cc1cc(OCc2c(F)cccc2F)n2nc(C)c(C(=O)NCC(C)(CC[Si](C)(C)C)NC(=O)OCc3ccccc3)c2c1]

75 mg (0.19 mmol, purity 84%) of 7-[(2,6-difluorobenzyl)oxy]-2,5-dimethylpyrazolo[1,5-a]pyridine-3-carboxylic acid from Example 4A were initially charged together with 94 mg (0.25 mmol) of HATU and 99 µl (0.57 mmol) of N,N-diisopropylethylamine in 0.62 ml of DMF, and the mixture was stirred at room temperature for 20 min. Subsequently, 78 mg (0.25 mmol) of ent-benzyl-[1-amino-2-methyl-4-(trimethylsilyl)butan-2-yl]carbamate (enantiomer A) from Example 15A were added to the reaction solution and the mixture was stirred at RT overnight. 7 ml of water were then added to the mixture. The precipitate formed was filtered off, diluted with acetonitrile and water, TFA was added and the mixture was purified by preparative HPLC (RPI8 column, mobile phase: acetonitrile/water gradient with addition of 0.1% TFA). The product fractions were combined and concentrated. This gave 70 mg of the target compound (50% of theory).

LC-MS (Method 2): $R_t$=1.39 min

MS (ESpos): m/z=623 (M-TFA+H)$^+$

Example 19A ent-Benzyl {1-[({7-[(2,6-difluorobenzyl)oxy]-2,5-dimethylpyrazolo[1,5-a]pyridin-3-yl}carbonyl)amino]-2-methyl-4-(trimethylsilyl)butan-2-yl}carbamate (Enantiomer B)

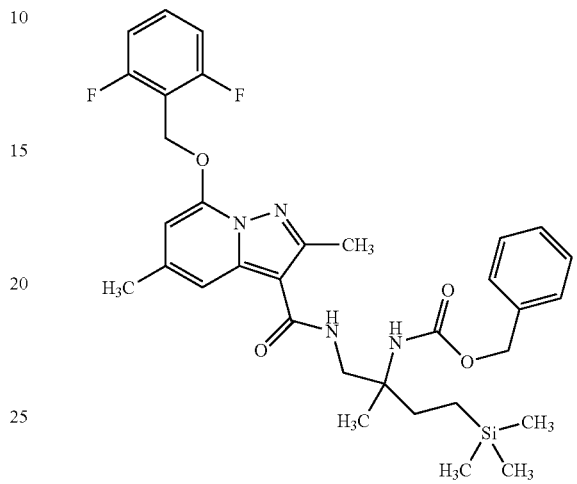

75 mg (0.19 mmol, purity 84%) of 7-[(2,6-difluorobenzyl)oxy]-2,5-dimethylpyrazolo[1,5-a]pyridine-3-carboxylic acid from Example 4A were initially charged together with 94 mg (0.25 mmol) of HATU and 99 µl (0.57 mmol) of N,N-diisopropylethylamine in 0.62 ml of DMF, and the mixture was stirred at room temperature for 20 min. Subsequently, 78 mg (0.25 mmol) of ent-benzyl-[1-amino-2-methyl-4-(trimethylsilyl)butan-2-yl]carbamate (enantiomer B) from Example 16A were added to the reaction solution and the mixture was stirred at RT for 2 h. Another 29 mg (0.095 mmol) of ent-benzyl-[1-amino-2-methyl-4-(trimethylsilyl)butan-2-yl]carbamate (enantiomer B) were added and the mixture was stirred at RT for 1 h. 7 ml of water were then added to the mixture. The precipitate formed was filtered off and dried under high vacuum. This gave 134 mg of the target compound (99% of theory, purity 88%).

LC-MS (Method 2): $R_t$=1.39 min

MS (ESpos): m/z=623 (M+H)$^+$

Example 20A rac-2-Amino-2-[2-(difluoromethyl)-2H-tetrazol-5-yl]propan-1-ol

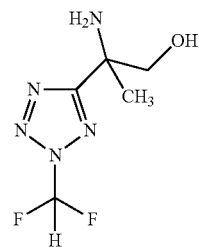

The target compound can be prepared by deprotection of 1-{[tert-butyl(dimethyl)silyl]oxy}-2-[2-(difluoromethyl)-

2H-tetrazol-5-yl]propane-2-amine (preparable analogously to intermediate 300 in WO2014/084312 from racemic starting material) using tetrabutylammonium fluoride (TBAF) in THF at room temperature, according to methods known from the literature.

WORKING EXAMPLES

Example 1

7-[(2,6-Difluorobenzyl)oxy]-N-[(2S)-1-hydroxy-2-(5-methyl-1,3,4-thiadiazol-2-yl)propan-2-yl]-2,5-dimethylpyrazolo[1,5-a]pyridine-3-carboxamide trifluoroacetate

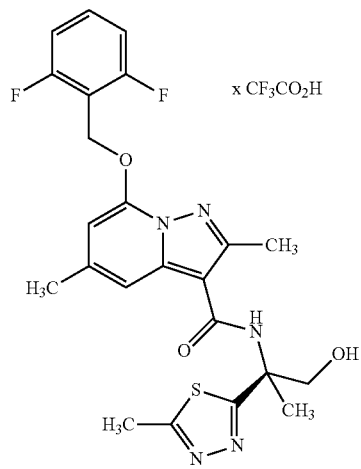 [SMILES: Cc1cc(OCc2c(F)cccc2F)n2nc(C)c(C(=O)N[C@@](C)(CO)c3nnc(C)s3)c2c1]

20 mg (0.05 mmol) of 7-[(2,6-difluorobenzyl)oxy]-2,5-dimethylpyrazolo[1,5-a]pyridine-3-carboxylic acid from Example 4A were initially charged together with 21 mg (0.06 mmol) of HATU and 70 µl (0.40 mmol) of N,N-diisopropylethylamine in 0.2 ml of DMF, and the mixture was stirred at room temperature for 10 min. 44 mg (0.15 mmol) of (2S)-2-amino-2-(5-methyl-1,3,4-thiadiazol-2-yl)propan-1-ol (preparable analogously to intermediate 307 in WO2014/084312) were then added to the reaction solution, and the mixture was stirred at RT for 2 h. The mixture was then stirred at 40° C. for 20 min and at 60° C. for 1.5 h. The mixture was then diluted with acetonitrile and water, TFA was added and the mixture was purified by preparative HPLC (RP18 column, mobile phase: acetonitrile/water gradient with addition of 0.1% TFA). The product fractions were combined and concentrated. This gave 10 mg of the target compound (31% of theory).

LC-MS (Method 2): $R_t$=0.89 min

MS (ESpos): m/z=488 (M-TFA+H)+

$^1$H-NMR (400 MHz, DMSO-$d_6$): δ=1.81 (s, 3H), 2.40 (s, 3H), 2.68 (s, 3H), 3.77-3.85 (m, 2H), 5.46 (s, 2H), 6.58 (s, 1H), 7.21-7.30 (m, 2H), 7.35 (s, 1H), 7.57-7.67 (m, 2H), [further signal hidden under solvent peak].

Example 2 rac-7-[(2,6-Difluorobenzyl)oxy]-N-{2-[2-(difluoromethyl)-2H-tetrazol-5-yl]-1-hydroxypropan-2-yl}-2,5-dimethylpyrazolo[1,5-a]pyridine-3-carboxamide

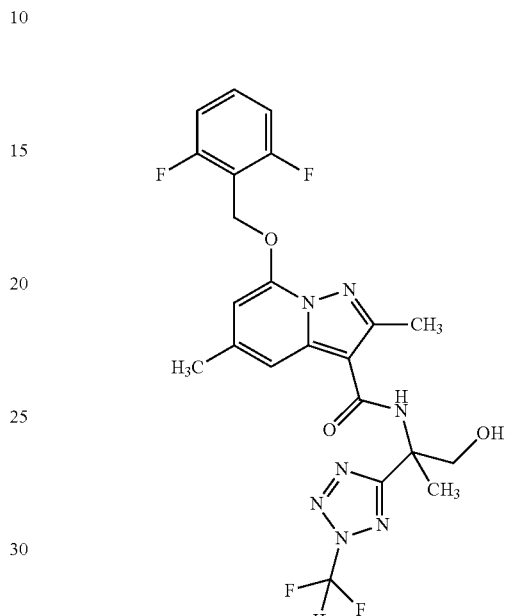

40 mg (0.10 mmol) of 7-[(2,6-difluorobenzyl)oxy]-2,5-dimethylpyrazolo[1,5-a]pyridine-3-carboxylic acid from Example 4A were initially charged together with 40 mg (0.11 mmol) of HATU and 88 µl (0.51 mmol) of N,N-diisopropylethylamine in 0.4 ml of DMF, and the mixture was stirred at room temperature for 10 min. 21 mg (0.11 mmol) of rac-2-amino-2-[2-(difluoromethyl)-2H-tetrazol-5-yl]propan-1-ol Example 20A were then added to the reaction solution, and the mixture was stirred at 60° C. for 6 h. The mixture was then diluted with acetonitrile and water, TFA was added and the mixture was purified by preparative HPLC (RP18 column, mobile phase: acetonitrile/water gradient with addition of 0.1% TFA). The product fractions were combined and concentrated. Subsequently, the residue was taken up in dichloromethane and a little methanol, and washed twice with saturated aqueous sodium bicarbonate solution. The aqueous phase was extracted twice with dichloromethane. The combined organic phases were dried over sodium sulfate, filtered, concentrated and lyophilized. This gave 40 mg of the target compound (74% of theory, purity 95%).

LC-MS (Method 2): $R_t$=0.98 min

MS (ESpos): m/z=508 (M+H)$^+$ $^1$H-NMR (400 MHz, DMSO-$d_6$): δ=1.83 (s, 3H), 2.40 (s, 3H), 3.79-3.88 (m, 2H), 5.32 (t, 1H), 5.46 (s, 2H), 6.57 (s, 1H), 7.21-7.30 (m, 2H), 7.31 (s, 1H), 7.57-7.67 (m, 2H), 8.56 (t, 1H), [further signal hidden under solvent peak].

Example 3 ent-N-[2-Amino-2-methyl(4,4,4-²H₃)butyl]-7-[(2,6-difluorobenzyl)oxy]-2,5-dimethylpyrazolo[1,5-a]pyridine-3-carboxamide (Enantiomer A)

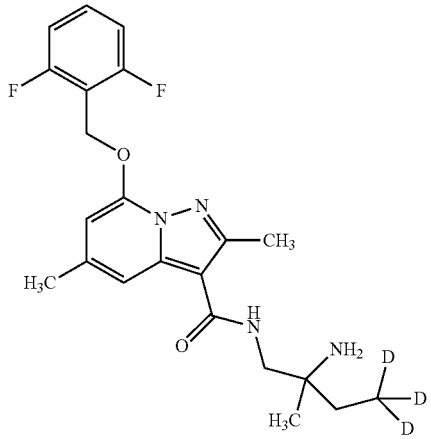 [SMILES: [2H]C([2H])([2H])CC(C)(N)CNC(=O)c1c(C)nn2c(OCc3c(F)cccc3F)cc(C)cc12]

111 mg (0.15 mmol, purity 76%) of ent-benzyl {1-[({7-[(2,6-difluorobenzyl)oxy]-2,5-dimethylpyrazolo[1,5-a]pyridin-3-yl}carbonyl)amino]-2-methyl(4,4,4-²H₃)butan-2-yl}carbamate (enantiomer A) from Example 17A were dissolved in 4 ml of ethanol, and 59 µl (0.76 mmol) of TFA and 5 mg (0.005 mmol) of 10% palladium on activated carbon were added under argon and the mixture was hydrogenated at standard pressure for 3.5 hours. The reaction solution was filtered using a Millipore filter and washed with ethanol, and the filtrate was concentrated using a rotary evaporator. Acetonitrile, water and TFA were added to the residue and the product was purified by preparative HPLC (RP18 column, mobile phase: acetonitrile/water gradient with addition of 0.1% TFA). The product fractions were combined and concentrated. Subsequently, the residue was taken up in dichloromethane and a little methanol, and washed twice with saturated aqueous sodium bicarbonate solution. The aqueous phase was extracted twice with dichloromethane. The combined organic phases were dried over sodium sulfate, filtered and concentrated. The residue was purified again by thick-layer chromatography (mobile phase: dichloromethane/2N ammonia in methanol=15/1). This gave 32 mg of the target compound (50% of theory).

LC-MS (Method 2): $R_t$=0.70 min

MS (ESpos): m/z=420 (M+H)⁺

¹H-NMR (500 MHz, DMSO-d₆): δ=0.96 (s, 3H), 1.27-1.38 (m, 2H), 1.48 (br. s, 2H), 2.39 (s, 3H), 3.10-3.22 (m, 2H), 5.46 (s, 2H), 6.55 (s, 1H), 7.20 (t, 1H), 7.23-7.29 (m, 2H), 7.39 (s, 1H), 7.58-7.67 (m, 1H), [further signal hidden under solvent peak].

Example 4 ent-N-[2-Amino-2-methyl-4-(trimethylsilyl)butyl]-7-[(2,6-difluorobenzyl)oxy]-2,5-dimethylpyrazolo[1,5-a]pyridine-3-carboxamide (Enantiomer A)

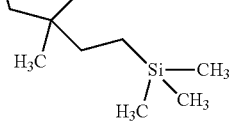

70 mg (0.09 mmol) of ent-benzyl {1-[({7-[(2,6-difluorobenzyl)oxy]-2,5-dimethylpyrazolo[1,5-a]pyridin-3-yl}carbonyl)amino]-2-methyl-4-(trimethylsilyl)butan-2-yl}carbamate trifluoroacetate (enantiomer A) from Example 18A were dissolved in 2.5 ml of ethanol, and 36 µl (0.47 mmol) of TFA and 3 mg (0.003 mmol) of 10% palladium on activated carbon were added under argon and the mixture was hydrogenated at standard pressure for 2 hours. The reaction solution was filtered using a Millipore filter and washed with ethanol, and the filtrate was concentrated using a rotary evaporator. The residue was purified by thick-layer chromatography (mobile phase: dichloromethane/2N ammonia in methanol=20/1). Subsequently, the residue was taken up in dichloromethane and a little methanol, and washed twice with saturated aqueous sodium bicarbonate solution. The aqueous phase was extracted twice with dichloromethane. The combined organic phases were dried over sodium sulfate, filtered and concentrated. This gave 30 mg of the target compound (65% of theory).

LC-MS (Method 2): $R_t$=0.87 min

MS (ESpos): m/z=489 (M+H)⁺

¹H-NMR (500 MHz, DMSO-d₆): δ=−0.04 (s, 9H), 0.43-0.57 (m, 2H), 0.96 (s, 3H), 1.25-1.37 (m, 2H), 1.85 (br. s, 2H), 2.40 (s, 3H), 3.16-3.23 (m, 2H), 5.46 (s, 2H), 6.55 (s, 1H), 7.21 (t, 1H), 7.22-7.29 (m, 2H), 7.38 (s, 1H), 7.58-7.67 (m, 1H), [further signal hidden under solvent peak].

Example 5 ent-N-[2-Amino-2-methyl-4-(trimethylsilyl)butyl]-7-[(2,6-difluorobenzyl)oxy]-2,5-dimethylpyrazolo[1,5-a]pyridine-3-carboxamide (Enantiomer B)

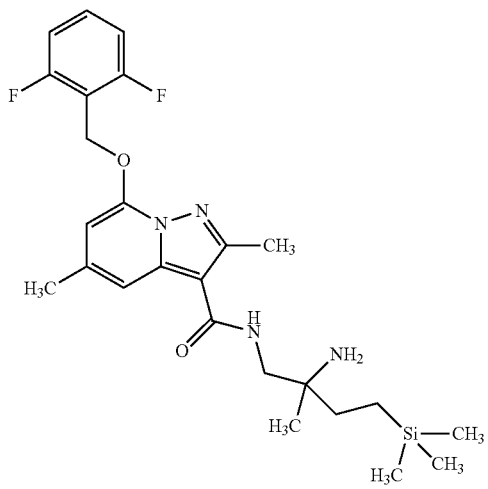 [SMILES: Cc1cc(OCc2c(F)cccc2F)n2nc(C)c(C(=O)NCC(C)(N)CC[Si](C)(C)C)c2c1]

134 mg (0.19 mmol, purity 88%) of ent-benzyl {1-[({7-[(2,6-difluorobenzyl)oxy]-2,5-dimethylpyrazolo[1,5-a]pyridin-3-yl}carbonyl)amino]-2-methyl-4-(trimethylsilyl)butan-2-yl}carbamate (enantiomer B) from Example 19A were dissolved in 5 ml of ethanol, and 73 µl (0.95 mmol) of TFA and 6 mg (0.006 mmol) of 10% palladium on activated carbon were added under argon and the mixture was hydrogenated at standard pressure for 5 hours. The reaction solution was filtered using a Millipore filter and washed with ethanol, and the filtrate was concentrated using a rotary evaporator. Acetonitrile, water and TFA were added to the residue and the product was purified by preparative HPLC (RP18 column, mobile phase: acetonitrile/water gradient with addition of 0.1% TFA). The product fractions were combined and concentrated. Subsequently, the residue was taken up in dichloromethane and a little methanol, and washed twice with saturated aqueous sodium bicarbonate solution. The aqueous phase was extracted twice with dichloromethane. The combined organic phases were dried over sodium sulfate, filtered and concentrated. This gave 58 mg of the target compound (62% of theory).

LC-MS (Method 2): $R_t$=0.84 min

MS (ESpos): m/z=489 (M+H)$^+$ $^1$H-NMR (500 MHz, DMSO-d$_6$): δ=−0.04 (s, 9H), 0.43-0.57 (m, 2H), 0.96 (s, 3H), 1.25-1.37 (m, 2H), 1.42 (br. s, 2H), 2.40 (s, 3H), 3.15-3.24 (m, 2H), 5.45 (s, 2H), 6.55 (s, 1H), 7.20 (t, 1H), 7.22-7.29 (m, 2H), 7.38 (s, 1H), 7.59-7.67 (m, 1H), [further signal hidden under solvent peak].

B. ASSESSMENT OF PHARMACOLOGICAL EFFICACY

The following abbreviations are used:
ATP adenosine triphosphate
Brij35 polyoxyethylene(23) lauryl ether
BSA bovine serum albumin:
DTT dithiothreitol
TEA triethanolamine The pharmacological action of the compounds of the invention can be demonstrated in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Conduct of the Test

To conduct the test, 29 µl of enzyme solution (0-10 nM soluble guanylyl cyclase (prepared according to Honicka et al., Journal of Molecular Medicine 77 (1999) 14-23), in 50 mM TEA, 2 mM magnesium chloride, 0.1% BSA (fraction V), 0.005% Brij 35, pH 7.5) were initially charged in the microplate, and 1 µl of the stimulator solution (0-10 µM 3-morpholinosydnonimine, SIN-1, Merck in DMSO) was added. The microplate was incubated at RT for 10 min. Then 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 µl of substrate solution (1.25 mM guanosine 5'-triphosphate (Sigma) in 50 mM TEA, 2 mM magnesium chloride, 0.1% BSA (fraction V), 0.005% Brij 35, pH 7.5) and analysed continuously in a luminometer.

B-2. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative MEC values (MEC=minimum effective concentration) for the compounds of the invention are shown in the table below (in some cases as mean values from individual determinations):

TABLE A

| Example | MEC [µM] |
|---|---|
| 1 | 0.20 |
| 2 | 0.10 |
| 3 | 0.30 |
| 4 | 0.53 |
| 5 | 0.30 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each in mM): sodium chloride: 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To generate a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor: APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed here to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

LITERATURE

Klaus Witte, Kai Hu, Johanna Swiatek, Claudia Müssig, Georg Ertl and Bjöm Lemmer: Experimental heart failure in rats: effects on cardiovascular circadian rhythms and on myocardial f-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is carried out by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is carried out at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it is stored at −20° C. until further processing.

An internal standard (which may also be a chemically unrelated substance) is added to the samples of the compounds of the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds of the invention were incubated with a concentration of about 0.1-10 µM. To this end, stock solutions of the compounds of the invention having a concentration of 0.01-1 mM in acetonitrile were prepared, and then pipetted with a 1:100 dilution into the incubation mixture. The liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h the incubation mixtures were stopped with acetonitrile (final concentration about 30%) and the protein was centrifuged off at about 15 000×g. The samples thus stopped were either analyzed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-8. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen und Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analyzed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrhythmias, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany). NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 μmol/l) (exposure about 5-6 minutes per concentration), followed by several washing steps.

The amplitude of the inward "tail" current which is generated by a change in potential from +20 mV to −120 mV serves to quantify the hERG potassium current, and is described as a function of time (IgorPro™ Software). The current amplitude at the end of various time intervals (for example stabilization phase before test substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011: 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998: 74:230-241.

The invention claimed is:
1. Compound of the formula (I)

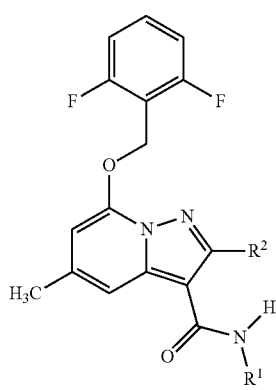

(I)

in which
$R^1$ represents a group of the formula

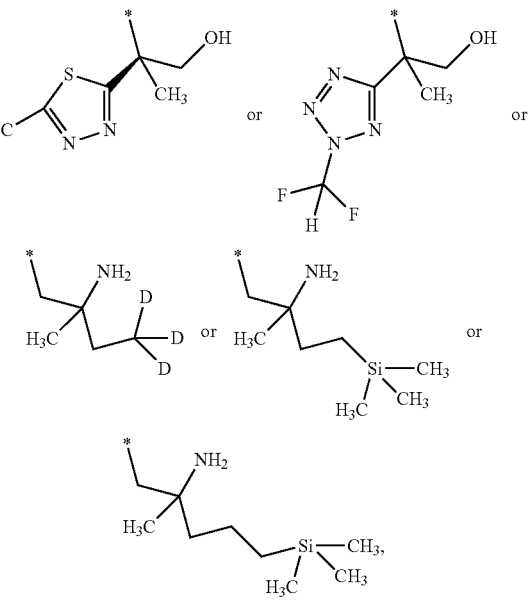

where * represents the point of attachment to the nitrogen atom, $R^2$ represents methyl or cyclopropyl,
and salts thereof.

2. The compound of the formula (I) as claimed in claim 1 in which
$R^1$ represents a group of the formula

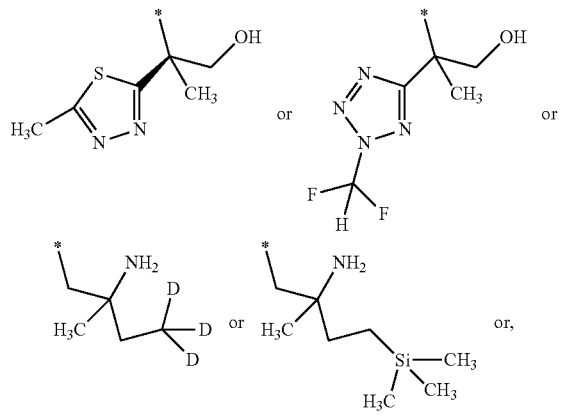

where * represents the point of attachment to the nitrogen atom, $R^2$ represents methyl,
and salts thereof.

3. The compound as claimed in claim 1 having the systematic name ent-7-[(2,6-difluorobenzyl)oxy]-N-[(2S)-1-hydroxy-2-(5-methyl-1,3,4-thiadiazol-2-yl)propan-2-yl]-2,5-dimethylpyrazolo[1,5-a]pyridine-3-carboxamide and the structural formula

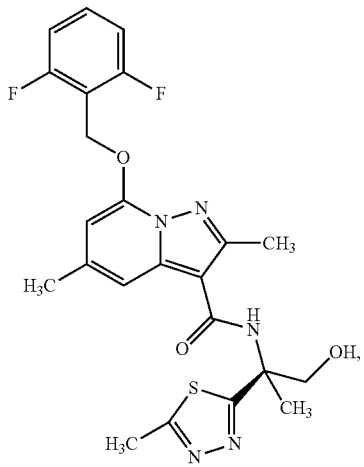 [SMILES: Cc1cc(OCc2c(F)cccc2F)n2nc(C)c(C(=O)N[C@@](C)(CO)c3nnc(C)s3)c2c1]

and salts thereof.

4. The compound as claimed in claim 1 having the systematic name rac-7-[(2,6-difluorobenzyl)oxy]-N-{2-[2-(difluoromethyl)-2H-tetrazol-5-yl]-1-hydroxypropan-2-yl}-2,5-dimethylpyrazolo[1,5-a]pyridine-3-carboxamide and the structural formula

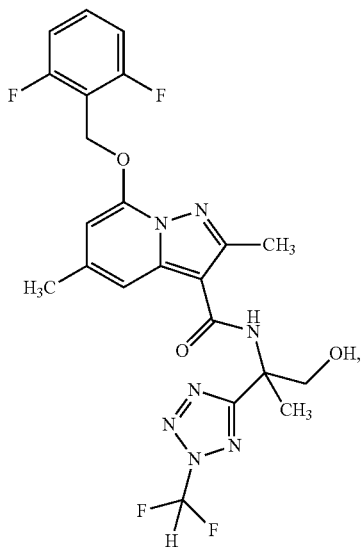 [SMILES: Cc1cc(OCc2c(F)cccc2F)n2nc(C)c(C(=O)NC(C)(CO)c3nnn(C(F)F)n3)c2c1]

and salts thereof.

5. The compound as claimed in claim 1 having the systematic name ent-N-[2-amino-2-methyl(4,4,4-2H3)butyl]-7-[(2,6-difluorobenzyl)oxy]-2,5-dimethylpyrazolo-[1,5-a]pyridine-3-carboxamide (enantiomer A) and the structural formula

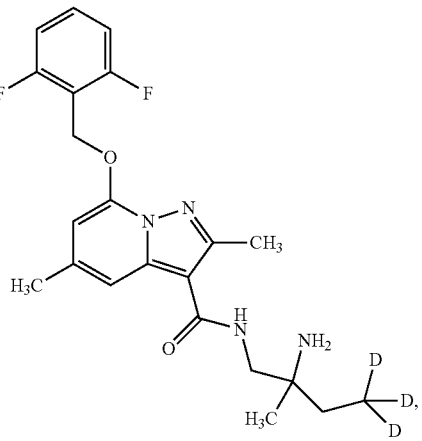

and salts thereof.

6. The compound as claimed in claim 1 having the systematic name ent-N-[2-amino-2-methyl-4-(trimethylsilyl)butyl]-7-[(2,6-difluorobenzyl)oxy]-2,5-dimethylpyrazolo[1,5-a]pyridine-3-carboxamide (enantiomer A) and the structural formula and salts thereof.

7. The compound as claimed in claim 1 having the systematic name ent-N-[2-amino-2-methyl-4-(trimethylsilyl)butyl]-7-[(2,6-difluorobenzyl)oxy]-2,5-dimethylpyrazolo[1,5-a]pyridine-3-carboxamide (enantiomer B) and the structural formula

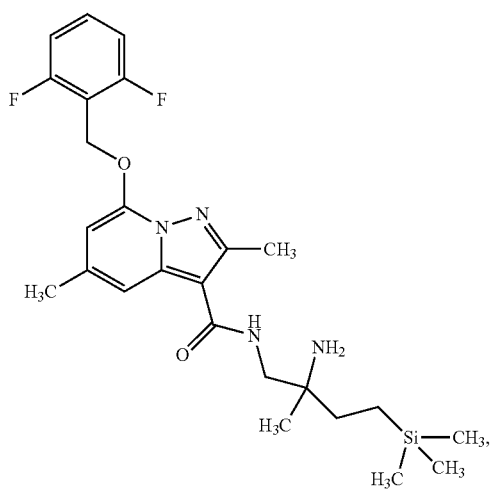 [SMILES: Cc1cc(OCc2c(F)cccc2F)n2nc(C)c(C(=O)NCC(C)(N)CC[Si](C)(C)C)c2c1]

and salts thereof.

8. A process for preparing compounds of the formula (I) as defined in claim 1, comprising reacting a compound of the formula (II)

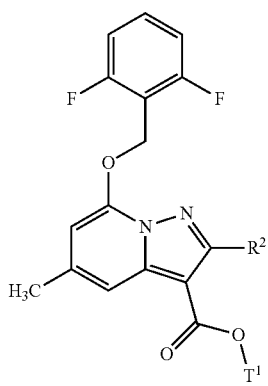
(II)

in which R² has the meaning given above and

T¹ represents (C₁-C₄)-alkyl or benzyl, in an inert solvent in the presence of a suitable base or acid to give a carboxylic acid of the formula (III)

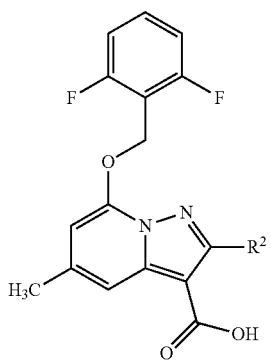
(III)

in which R² has the definition given above, and reacting the carboxylic acid of formula (III) in an inert solvent under amide coupling conditions, with an amine of the formula (IV-A), (IV-B), (IV-C) or (IV-D)

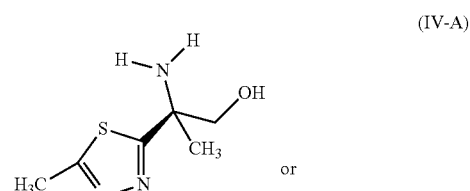
(IV-A)

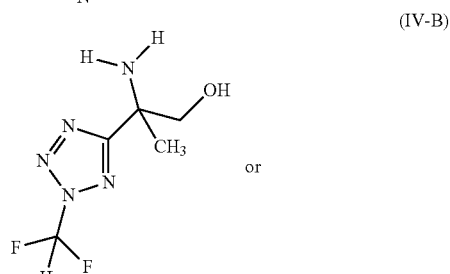
(IV-B)

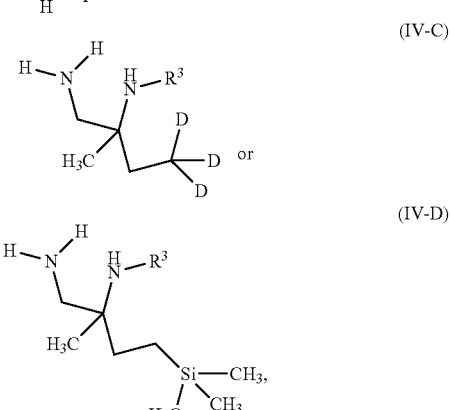
(IV-C)

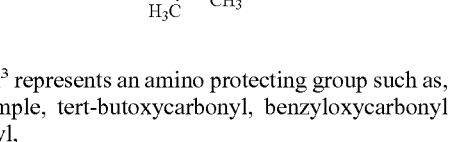
(IV-D)

in which R³ represents an amino protecting group such as, for example, tert-butoxycarbonyl, benzyloxycarbonyl or benzyl, then detaching any protective groups present optionally converting the resulting compounds of the formula (I) with the appropriate acids or bases to the salts thereof.

9. A medicament comprising the compound as defined in claim 1 in combination with one or more inert, nontoxic, pharmaceutically suitable excipients.

10. A medicament comprising the compound as defined in claim 1 in combination with a further active compound selected from the group consisting of organic nitrates, NO donors, cGMP-PDE inhibitors, antithrombotic agents, hypotensive agents and lipid metabolism modifiers.

11. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 1 to a human or animal in need thereof.

12. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 2 to a human or animal in need thereof.

13. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 3 to a human or animal in need thereof.

14. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 4 to a human or animal in need thereof.

15. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 5 to a human or animal in need thereof.

16. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 6 to a human or animal in need thereof.

17. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of at least one compound of claim 7 to a human or animal in need thereof.

18. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering an effective amount of the medicament of claim 9 to a human or animal in need thereof.

\* \* \* \* \*